(12) United States Patent
Kang et al.

(10) Patent No.: US 8,758,727 B2
(45) Date of Patent: Jun. 24, 2014

(54) SITE SPECIFIC FLUORESCENCE AND CONTRAST MARKER FOR SAME

(75) Inventors: Kyung A. Kang, Louisville, KY (US); Michael H. Nantz, Louisville, KY (US)

(73) Assignee: University of Louisville Research Foundation, Inc., Louisville, KY (US)

(*) Notice: Subject to any disclaimer, the term of this patent is extended or adjusted under 35 U.S.C. 154(b) by 633 days.

(21) Appl. No.: 12/935,336

(22) PCT Filed: Mar. 31, 2009

(86) PCT No.: PCT/US2009/039025
§ 371 (c)(1), (2), (4) Date: Jan. 3, 2011

(87) PCT Pub. No.: WO2009/139972
PCT Pub. Date: Nov. 19, 2009

(65) Prior Publication Data
US 2011/0104070 A1    May 5, 2011

Related U.S. Application Data

(60) Provisional application No. 61/072,427, filed on Mar. 31, 2008.

(51) Int. Cl.
*A61B 5/00* (2006.01)
*C12Q 1/02* (2006.01)

(52) U.S. Cl.
USPC .............................. 424/9.6; 435/7.1

(58) Field of Classification Search
None
See application file for complete search history.

(56) References Cited

U.S. PATENT DOCUMENTS

| | | | |
|---|---|---|---|
| 5,466,439 A | 11/1995 | Gibby et al. | |
| 6,083,486 A | 7/2000 | Weissleder et al. | |
| 6,312,906 B1 * | 11/2001 | Cass et al. | 435/6.11 |
| 7,011,817 B2 * | 3/2006 | Achilefu et al. | 424/9.6 |
| 7,883,900 B2 | 2/2011 | Kang | |
| 7,971,573 B2 | 7/2011 | Portin et al. | |
| 2004/0057903 A1 | 3/2004 | Hancu et al. | |

FOREIGN PATENT DOCUMENTS

| | | |
|---|---|---|
| WO | WO/2006/065146 | 6/2006 |
| WO | WO 2006064453 A2 * | 6/2006 |
| WO | WO/2006/102307 | 9/2006 |

OTHER PUBLICATIONS

Lee et al. A near-infrared-fluorescence-quenched gold-nanoparticle imaging probe for in vivo drug screening and protease activity determination. 2008 Angew. Chem. Int. Ed. 47: 2804-2807. Published online Feb. 27, 2008.*

Schmalfeldt et al. Increased expression of matrix metalloproteinases (MMP)-2, MMP-9, and the urokinase-type plasminogen activator is associated with progression from benign to advanced ovarian cancer. 2001 Clin. Cancer Res. 7: 2396-2404.*

Chung et al. Development of a novel albumin-binding prodrug that is cleaved by urokinase-type-plasminogen activator (uPA). 2006 Bioorg. Med. Chem. Lett. 16: 5157-5163.*

Achilefu, S., et al., "Novel Receptor-Targeted Fluorescent Contrast Agents for In Vivo Tumor Imaging," Investigative Radiology, vol. 35, No. 8, 479-485, 2000.

Geddes, C.D., et al., "Enhanced photostability of ICG in close proximity to gold colloids," Spectrochimica Acta Part A: 59, 2611-2617 (2003).

Hong, B., et al., "Biocompatible, nanogold-particle fluorescence enhancer for fluorophore mediated, optical immunosensor," Biosensors and Bioelectronics 21 (2006) 1333-1338.

Hong B., et al., "Fluorescence Enhancers for Fluorophore Mediated Biosensors for Cardiovascular Disease Diagnosis," Advances in Experimental Medicine and Biology, vol. 578: 179-184 (2006).

Hranisavljevic, J., et al., "Photoinduced Charge Separation Reactions of J-Aggregates Coated on Silver Nanoparticles," J. Am. Chem. Soc. 2002, 124, 4536-4537.

Kang, K.A., et al., "Biocompatible Nanometal Particle Fluorescence Enhancers," Critical Review in Eukaryotic Gene Expression, 16(1):45-60 (2006).

Licha, K., et al., "Hydrophilic Cyanine Dyes as Contrast Agents for Near-Infrared Tumor Imaging: Synthesis, Photophysical Properties and Spectroscopic In vivo Characterization," Photochemistry and Photobiology, 2000, 72(3): 392-398.

Ntziachristos, V., et al., "Probing physiology and molecular function using optical imaging: applications to breast cancer," Breast Cancer Res 2001, 3:41-46.

Ruppin, R., "Optical absorption by a small sphere above a substrate with inclusion of nonlocal effects," Physical Review B, vol. 45, No. 19, 11 209-11 215, May 15, 1992.

* cited by examiner

*Primary Examiner* — Michael G Hartley
*Assistant Examiner* — Jennifer Lamberski
(74) *Attorney, Agent, or Firm* — Greer, Burns & Crain, Ltd.

(57) ABSTRACT

A contrast marker for indicating a presence of a target cell in an environment comprises a fluorophore, an NMP, and a short spacer and a long spacer linking the fluorophore to the NMP. The short spacer holds the fluorophore at a quenching distance from the NMP and the long spacer holds the fluorophore at a fluorescence enhancing distance from the NMP. The short spacer is configured to be cleaved by a molecule characterizing the target cells.

17 Claims, 22 Drawing Sheets

(1) Cypate is not conjugated to an NMP
(2) Cypate is conjugated to an NMP via an 8-amino acid peptide chain.

US 8,758,727 B2

SITE SPECIFIC FLUORESCENCE AND CONTRAST MARKER FOR SAME

PRIORITY CLAIM AND REFERENCE TO RELATED APPLICATION

This application claims the benefit of U.S. Provisional Application Ser. No. 61/072,427, filed Mar. 31, 2008, under 35 U.S.C. §119 and/or 35 U.S.C. §120, which is incorporated by reference herein.

STATEMENT OF GOVERNMENT INTEREST

This invention was made with government support under DOD Grant No. W81XWH-08-1-0460 awarded by Department of Defense (DOD). The government has certain rights in the invention.

TECHNICAL FIELD

A field of the invention is biosensing and medical imaging. Example applications of the invention include fluorescence detection of breast cancer and other cancers with a site specific enhanced fluorescence molecule.

BACKGROUND ART

In bioimaging, characterization, e.g., detection and/or diagnosis of particular cells within an environment, such as within a patient, is useful for many reasons as will be appreciated in the art. However, widely used methods for characterization of cells have certain drawbacks.

As a nonlimiting example, X-ray mammography is a known method for breast cancer detection, but X-ray mammography has low sensitivity for younger women (e.g., <40 years) due to their dense breast tissue. An X-ray mammogram can identify a suspected tumor in younger women, but invasive removal of tissue is needed from the suspected region for a biopsy to determine whether the tissue is cancerous or benign.

A more recent, and less invasive, technique for breast cancer detection is optical mammography. This technique uses near infrared (NIR) light to identify concentrated amounts of hemoglobin. Tumors generate blood vessels and therefore tend to have more blood and more hemoglobin, which is a natural but strong chromophore in tissue. This results in high absorption of NIR light. Optical mammography methods can detect tumors as small as 0.5 mm.

However, this technique can fail to identify tumors that are particularly small or deep-seated within the breast. Such tumors have weak optical contrast and are still difficult to detect. In the case of very small and/or deeply seated tumors, additional contrast may be needed for detection. Such additional contrast can be achieved by using fluorescing contrast markers.

DISCLOSURE OF THE INVENTION

According to embodiments of the present invention, a contrast marker is provided for indicating a presence of a target cell in an environment. The contrast marker comprises a fluorophore, a nano-sized metal particle (NMP), and a short spacer and a long spacer linking the fluorophore to the NMP. The short spacer holds the fluorophore at a quenching distance from the NMP and the long spacer holds the fluorophore at a fluorescence enhancing distance from the NMP. The short spacer is configured to be cleaved by molecules characterizing the target cells. Before the short spacer is cleaved, the short spacer controls a distance between the fluorophore and the NMP to be a quenching distance. After the short spacer is cleaved, the long spacer controls the distance between the fluorophore and the NMP to be a fluorescence enhancing distance.

BEST MODE OF CARRYING OUT THE INVENTION

Figure 1:
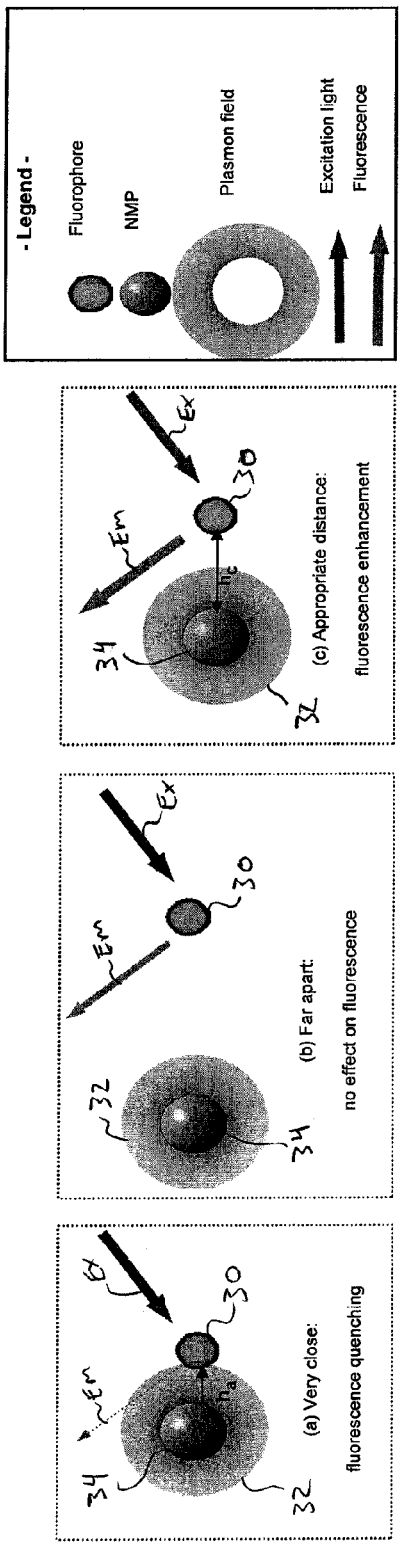
FIG. 1 shows an effect of a nano-sized metal particle (NMP) on fluorescence of a fluorophore at various distances.

Fluorophore mediated molecular imaging is highly beneficial for understanding mechanisms of various biomolecular functions. Fluorophores have a unique property of absorbing a particular wavelength of light and emitting light at another wavelength. Therefore, the optical noise originating from the tissue can be suppressed. Accordingly, fluorophores have been used for various methods of disease diagnosing and monitoring, such as but not limited to observing blood vessels in the heart or the retina in eyes.

Fluorophores have also been used as a contrast marker in cancer characterization, such as but not limited to breast cancer diagnosis, and also for understanding various biomolecular phenomena involved in breast cancer. Highly specific and sensitive recognition of breast cancer biomarkers is important for accurate and early diagnosis of the cancer. Targeting these biomarkers with fluorophore-mediated contrast agents that emit light only at cancer sites can maximize the tumor contrast with a low, background fluorescence from surrounding normal tissues.

Currently, there are only a limited number of fluorophores that can be used in humans. For in vivo bioimaging, such as cancer characterization, the fluorophore must be non-toxic. Further, fluorophores with excitation and emission in a near infrared (NIR) range have advantages over those in a visible range. This is because NIR can be better differentiated from the naturally occurring fluorescence in tissue and because NIR penetrates deeper into tissue.

Most of these fluorophores, however, have a low quantum yield (QY), a result of a molecular structure in which excited electrons are often paired with lone pair electrons without being used for fluorescence emission. This phenomenon is often called "self quenching" of fluorescence. Fluorophores with high QY are highly desirable, especially for detecting small and/or deeply seated tumors.

In order for a molecular imaging to be highly effective, the fluorescence contrast should be maximized at the target cell site (e.g., tumor site), with a minimal non-specific emission. A good approach, therefore, is using an entity with conditional emission. According to example embodiments of the present invention, by causing fluorophores to shine light only at the site of target cells, the diagnosis of such cells can be made much more sensitive and accurate. Thus, it is useful for a contrast marker to provide enhanced fluorescence, while also providing specificity with regard to a target cell.

Embodiments of the present invention take advantage of fluorophore properties to provide an improved contrast marker designed to be conditionally emitted only at a particular target cell site (e.g., a particular tumor site), at an enhanced fluorescence level. Since fluorophores emit fluorescence when their electrons are excited by photons, their fluorescence may be altered when they are placed within a strong surface plasmon polarion field (SPPF) (plasmon field) of nano sized metal particles (NMPs). Gold, silver, and platinum are nonlimiting examples of metals possessing strong SPPF. When the NMP's electrons couple with excited electrons of a fluorophore, an instantaneous electron attraction occurs, altering the energy states of the electrons involved in fluorescence emission. The level of this alteration depends on the strength of the SPPF where the fluorophore is placed, and the field strength depends on the metal type, NMP size, and distance from the NMP surface.

More particularly, if a fluorophore is placed within a very strong SPPF, most electrons of the fluorophore, including the ones for fluorescence emission, are attracted to the NMP, resulting in fluorescence quenching If the fluorophore is at a particular distance from the NMP, and attracts the electrons participating in self-quenching, then the fluorescence is enhanced.

According to example embodiments and methods of the present invention, this property of NMP's influence on a fluorophore can be effectively utilized for artificial fluorescence alteration. An example contrast marker and bioimaging method according to embodiments of the present invention uses NMPs, such as but not limited to nanogold particles (NGPs), to provide a fluorescent contrast agent that is highly site specific to a target cell. The fluorescence of the fluorophore is manipulated by placing two spacers, one relatively shorter (short spacer) and one relatively longer (long spacer), between the fluorophore and the NMP, linking the fluorophore and the NMP.

According to more particular example embodiments, contrast markers of the invention include a short spacer that places the fluorophore at a distance that forces the fluorescence to be completely quenched (or nearly completely quenched). Additionally, the short spacer includes a biological moiety that is cleaved by a molecule characterizing the target cell, such as but not limited to an enzyme secreted by target cells. The long spacer, on the other hand, is comparatively biologically stable, and it places the fluorophores at a distance where the NMP can enhance the fluorescence extensively.

The contrast marker can be configured specifically for a particular target cell by, for example, providing a targeting biomolecule that interfaces with the target cell, and providing a short spacer that is cleaved by the molecule characterizing the target cell, such as an enzyme secreted by the desired target cell. In this way, customized medicine can be provided.

A nonlimiting example embodiment of the invention is a cancer contrast marker with enhanced fluorescence only when the contrast marker attaches to a cancer site. The fluorescence enhancement is quenched at other times. This example contrast marker of the invention ensures specificity by at least two mechanisms, i.e., the targeting biomolecule and a target cell dependent enzyme, minimizing the noise usually caused by misplacement in normal tissues. However, it is to be understood that even though example embodiments of the present invention are discussed with respect to a cancer contrast marker for illustrative purposes, contrast markers according to embodiments of the present invention can be provided for targeting other cells and/or sites as well.

As a nonlimiting example, a contrast marker according to embodiments of the present invention designed for targeting breast cancer does not emit fluorescence, or exhibits highly quenched fluorescence, at sites without breast cancer cells, because the shorter spacer ensures fluorescence quenching. When this example contrast marker arrives at a cancer site, the shorter spacer gets cleaved by the enzyme secreted by the cancer cells. This forces the NMP-fluorophore distance to be at a length of the long spacer, allowing extensive fluorescence enhancement.

Highly specific and sensitive recognition of cancer (e.g., breast cancer) biomarkers is important for accurate and early diagnosis of the cancer. Targeting these biomarkers with fluorophore-mediated contrast agents that emit light only at cancer sites can provide desirable specificity, maximizing the tumor contrast by providing enhanced fluorescence at the cancer site with a low, background fluorescence from surrounding normal tissues.

Using such an example contrast marker of the present invention, the breast cancer can be characterized non-invasively (by optical mammography), earlier (with a higher sensitivity by enhanced fluorescence), and with a higher accuracy (the cleaving site can be customized for each cancer-representing enzyme). However, those in the art will thus appreciate that contrast markers of the present invention can be provided and used for characterizing other cancers and/or other diseases, as well as in research for understanding behavior of various bio-molecules.

Fluorophore selection for contrast markers can be based on various factors. For example, Indocyanine Green (ICG, MW 775) is one of a few FDA-approved fluorophores. Its maximal excitation and emission wavelengths are at 780 and 830 nm (both in NIR), respectively. Unfortunately, the quantum yield of ICG is only 0.0028 in a saline buffer and 0.012 in blood. Because ICG does not have a functional group amenable to biological conjugation, an ICG derivative, Cypate, is provided with two carboxylic acid groups.

Thus, a preferred cancer contrast marker of the invention uses a fluorophore, for example Cypate, linked to a nanometal particle (NMP) by both a short spacer and a long spacer. The short spacer holds the fluorophore at a quenching distance from the NMP but is cleaved by molecules that characterize cancer cells, which in an example embodiment may be enzymes secreted by cancer cells. Upon cleaving of the short spacer, the long spacer then controls the distance of the fluorophore relative to the NMP to produce a fluorescence enhancement. Example NMPs include a nanogold particle (NGP), nanosilver particle, or nanoplatinum particle.

An example contrast marker of the invention for breast cancer detection ensures the fluorescence contrast only for the cancer by the dual mechanisms of (a) targeting breast cancer receptors and (b) utilizing an enzyme secreted by breast cancer cells. Thus, the example contrast marker significantly increases the specificity for the cancer, with minimal noise that may otherwise come from the locators placed at sites other than the cancer.

An example contrast marker of the invention provides a much higher quantum yield than a fluorophore (e.g., Cypate) alone, at the cancer site. This in turn enables more sensitive, specific, and accurate NIR optical mammography. By varying the combination of the cancer targeting biomolecule and/or the characterizing molecule of the target cell, the cancer (e.g., breast cancer) can not only be located, but also be diagnosed. Example contrast markers of the invention can be used, for example, for breast cancer detection, but contrast markers of the invention can also be used for other cancer detection/diagnosis or even other disease diagnosis. Additionally, the NMP used in a marker of the invention can also include therapeutic moieties, such as a cancer treating drug, to enable both cancer detection/diagnosis and treatment.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

Example embodiments of the present invention allow manipulation of the light emission level from a fluorophore, utilizing the high surface-plasmon density of nano-sized metal particles (NMP). An NMP can quench fluorescence when it is placed close to a fluorophore, and it can enhance fluorescence extensively when located at a few nanometers from a fluorophore. This phenomenon is due to the surface plasmon polarion field (SPPF) (plasmon field) effects of an NMP. When the SPPF of an NMP is sufficiently strong, then it can attract a fluorophore's lone pair electrons and alter fluorescence emission significantly. Gold, silver, and platinum are good exemplary metals possessing a strong SPPF because of their unique atomic structure of high electron density in outer shells. For in vivo characterization, the NMPs should be non-cytotoxic metal. However, for other characterization (ex vivo applications, etc.), this may not be required.

The mechanism of altering fluorescence by nanoparticles of these metals is as follows. When oscillating electrons in the SPPF of an NMP couple with excited electrons of a fluorophore, an instantaneous electron attraction (possibly even an electron transfer) occurs from the fluorophore to the NMP, altering the energy states of the electrons involved in the fluorescence emission. The level of this alteration depends upon the strength of the plasmon field where the fluorophore is placed. The plasmon field strength depends upon the metal type, NMP size, and distance from the NMP surface.

For example, as shown in FIG. 1, when a fluorophore (or light emitting entity including quantum dots in general) 30 is placed near a strong SPPF 32 of an NMP 34, one of the following three situations occurs: 1) if the fluorophore 30 is placed within a distance $h_a$ very close to the NMP 34 and therefore is inside a high strength plasmon field 32, then most electrons, including those needed for fluorescence emission, are attracted to the NMP, resulting in partial or total fluorescence quenching (part (a)); 2) if the fluorophore 30 is away from the NMP 34 and outside the plasmon field 32, then there will be little change in the fluorescence (part (b)); 3) if the fluorophore 30 is at a particular distance $h_c$ from an NMP 34, where only the electrons that normally participate in self-quenching are attracted to the plasmon field 32, then the fluorescence is enhanced (part (c)).

Using this feature of NMPs, a highly target cell-specific, optical contrast agent with an excellent fluorescence quantum yield even in dense tissue (e.g., certain breast tissue) can be provided. Such a contrast agent includes a fluorophore-NMP, linked via two spacers, a relatively shorter spacer (short spacer) and a relatively longer spacer (long spacer). In the inventive contrast marker, the fluorophore is linked to the NMP via the short spacer, and the fluorescence is completely quenched when the short spacer is present.

Figure 2:
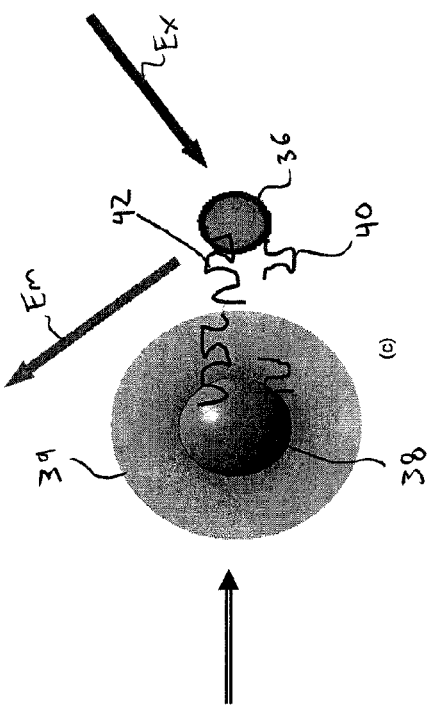
FIG. 2 shows an effect of cleaving a short spacer by a cancer enzyme according to an embodiment of the invention.
Figure 2:
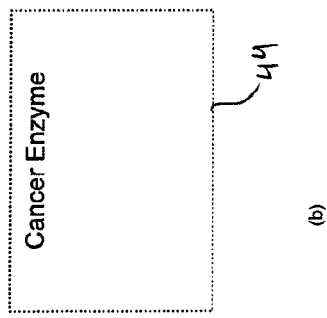
Figure 2:
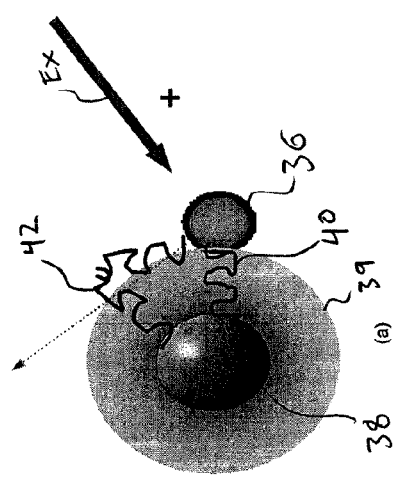

FIG. 2 at stage (a) shows an example fluorophore 36 and an NMP 38 (having a plasmon field 39) linked by a short spacer 40 and a long spacer 42. If both the short spacer 40 and the long spacer 42 link the fluorophore 36 to the NMP 38, then the short spacer controls the distance between them. An example of the effect of the NMP 38 when held very close to the fluorophore 36 by the short spacer 40 is shown at this stage. When the fluorophore 36 is linked to the NMP 38 via the short spacer 40, the fluorescence is mostly or completely quenched.

The short spacer 40 is one that is designed to be cleaved by a molecule characterizing the target cell, such as but not limited to an enzyme 44 (such as a cancer enzyme) secreted by target cells (such as cancer cells), so that the quenching effect ceases upon association of the contrast marker with the target cells. As described above, the longer spacer 42 is biologically stable and places the fluorophores 36 at a distance where the NMP 38 can extensively enhance the fluorescence. For example, as shown in stages (b) and (c) of FIG. 2, when the linked NMP-fluorophore arrives at a target cell site (e.g., cancer sites), the shorter spacer 40 gets cleaved by enzymes 44 produced by the target cells. This forces the NMP-fluorophore distance to be at a length of the long spacer 42, which length is optimized for fluorescence enhancement. An example of this extensive fluorophore enhancement is shown at stage (c).

Thus, an example contrast marker, when placed without targeted cells (e.g., breast cancer cells), does not emit fluorescence (or emits very limited fluorescence) because the shorter spacer ensures the fluorescence quenching When the entity arrives at the site of a target cell, the shorter spacer gets cleaved by enzymes produced by the target cells. This forces the NGP-fluorophore distance to be at a length of the long spacer, which is preferably optimized for fluorescence enhancement.

Figure 3:
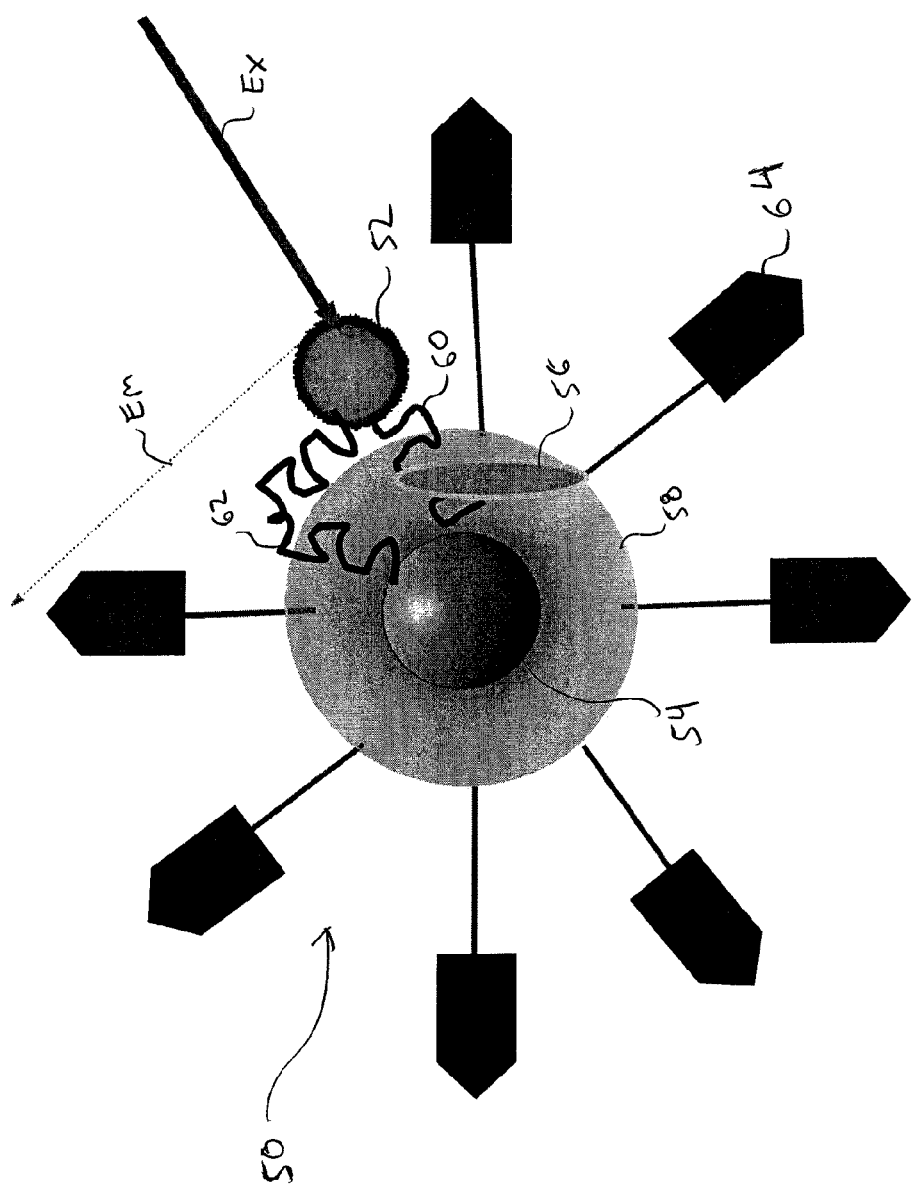
FIG. 3 shows an example contrast marker according to an embodiment of the invention.

FIG. 3 shows an example highly cancer-specific fluorescing contrast marker 50, which takes advantage of the relationship between a fluorophore 52 and a fluorophore enhancer (NMP) 54. This example contrast marker 50 enables both detection and diagnoses of cancer by using a proper enzyme 56, which is important for customized medical practice. An example contrast marker 50 can be a highly cancer specific, fluorescing nano-contrast marker for effective use in cancer detection and diagnosis. The same concept can be used in other embodiments of the invention for other disease diagnosis.

A nonlimiting fluorophore 52 used in the inventive contrast marker 50 is Cypate, as discussed above. In FIG. 3, the NMP (for example, embodied as a nanogold particle (NGP)) 54, having a strong plasmon field 58, is conjugated to Cypate 52 via two spacers, a short spacer 60 and a long spacer 62. The short spacer (short linker) 60 is provided for setting a distance between the NMP 54 and the fluorophore 52 for fluorescence quenching In other words, the short spacer (short linker) 60 is sufficiently short to ensure that Cypate fluorescence is quenched. The short spacer 60 is a structure designed to be cleaved by an enzyme 56 secreted by the cancer cell (in this example). More particularly, the short spacer includes a moiety that can be cleaved by the enzyme. To associate with the cancer cell, the NMP 54 is coated with a cancer targeting biomolecule 64. The long spacer (long linker) 62 is provided for setting a distance between the NMP 54 and the fluorophore 52 for fluorescence enhancement. Preferably, the length of the long spacer 62 is such that the fluorescence of the linked Cypate 52 is enhanced at a maximal level. Further, the long spacer 62 preferably is biocompatible and bio-chemically stable.

After administering to a patient and prior to locating a target site, the contrast marker 50 can emit little or no fluorescence because the short spacer 62 ensures that the fluorophore (e.g., Cypate) is within the strong plasmon field of the NMP, causing fluorescence quenching An example of this process is shown in FIGS. 4-7, which show stages in an example detection/diagnosis method using an example contrast marker 50 of the present invention.

Figure 4:
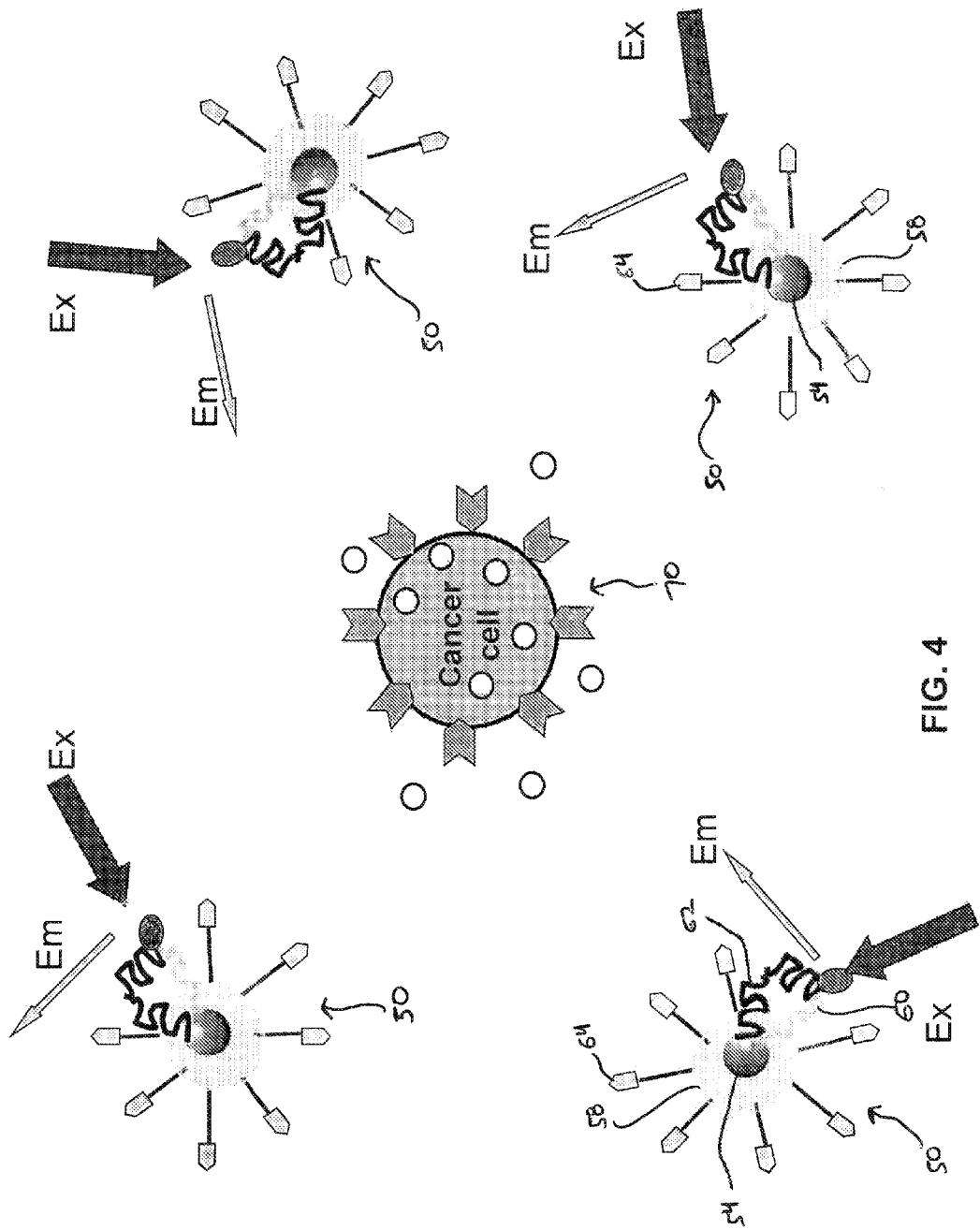
FIG. 4 shows a stage in operation of an inventive contrast marker, before the contrast marker reaches a cancer cell site.

The contrast marker 50, which as shown in FIG. 4, may include plural fluorophore-NMP complexes, is delivered into an environment, such as the blood stream of a patient, near the site of a suspected cancer cell 70 or other target cell. Prior to reaching the target site, as shown in FIG. 4, the short spacer 60 controls the distance between the NMP 54 and the fluorophore 52, so that fluorescence quenching is present. An excitation light Ex is applied to the contrast marker 50, for example, by a near-infrared spectrophotometer (which may also be used as a detector); however, fluorescence is quenched, resulting in a greatly reduced emitted light Em.

Figure 5:
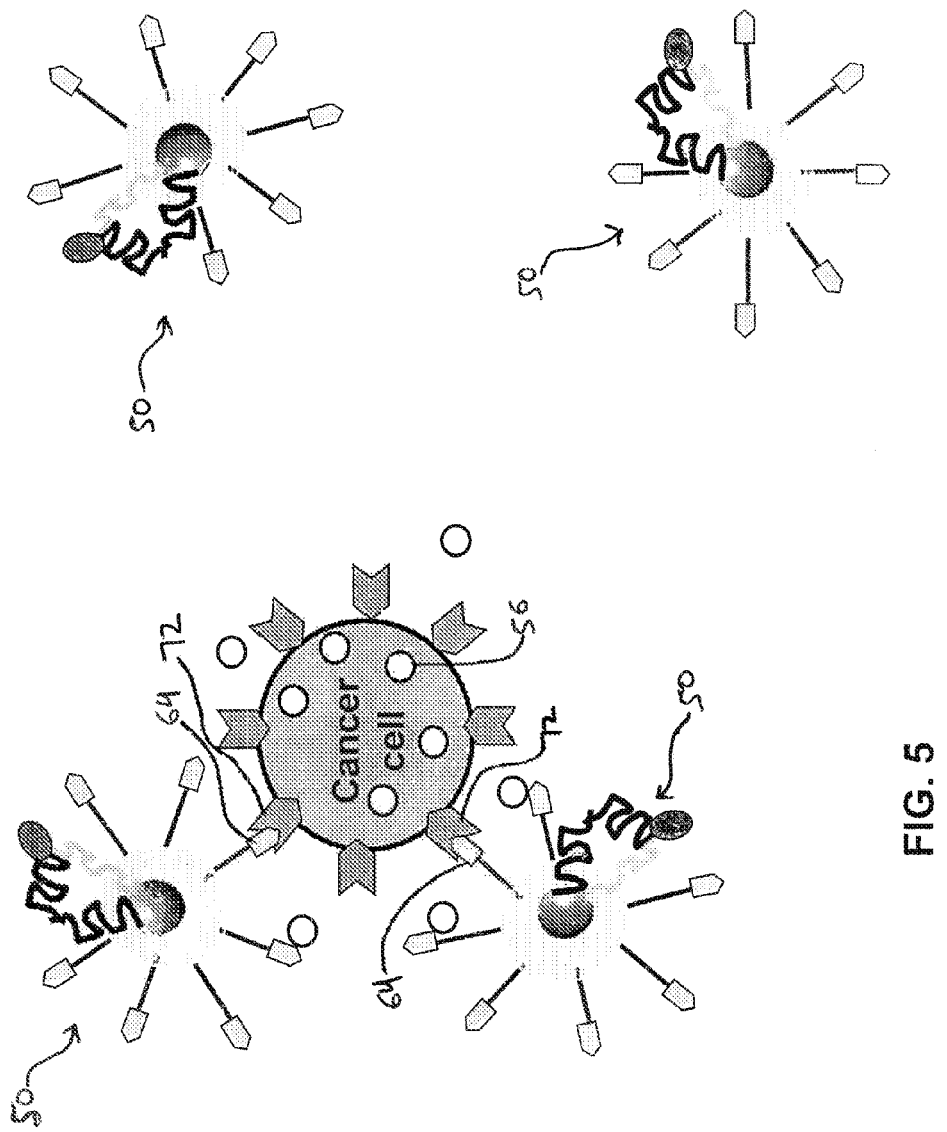
FIG. 5 shows a stage in operation of an inventive contrast marker, when the contrast marker reached the cancer cell site.

When one or more of the contrast marker complexes 50 reaches the site of the target cell 70, as shown in FIG. 5, the targeting molecule 64 on the contrast marker(s) reacts with the receptor 72 on the target cell. Other contrast marker complexes 50 may, for example, be washed out by the blood stream.

Figure 6:
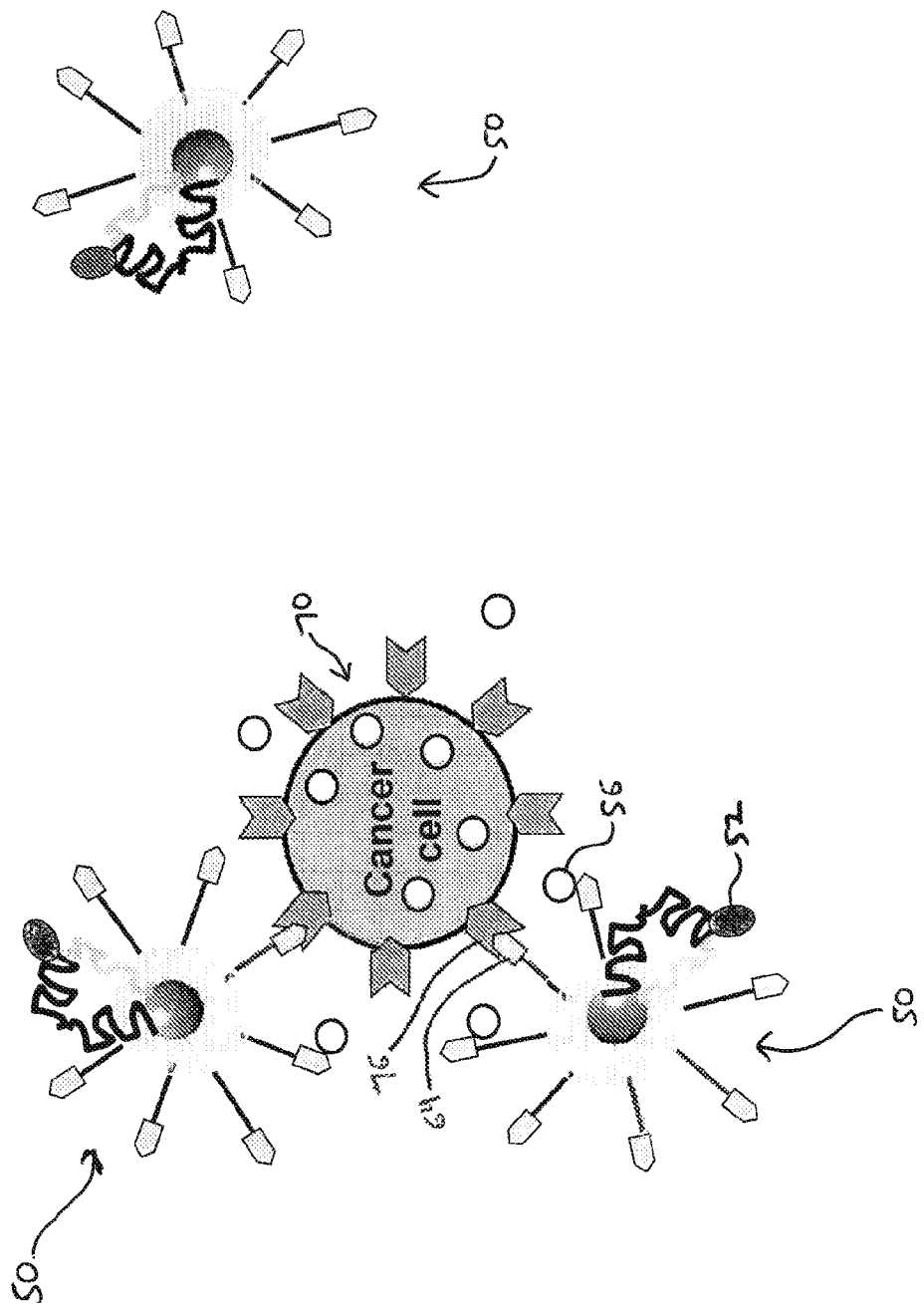
FIG. 6 shows a stage in operation of an inventive contrast marker, showing the contrast marker associating with the cancer cell.
Figure 7:
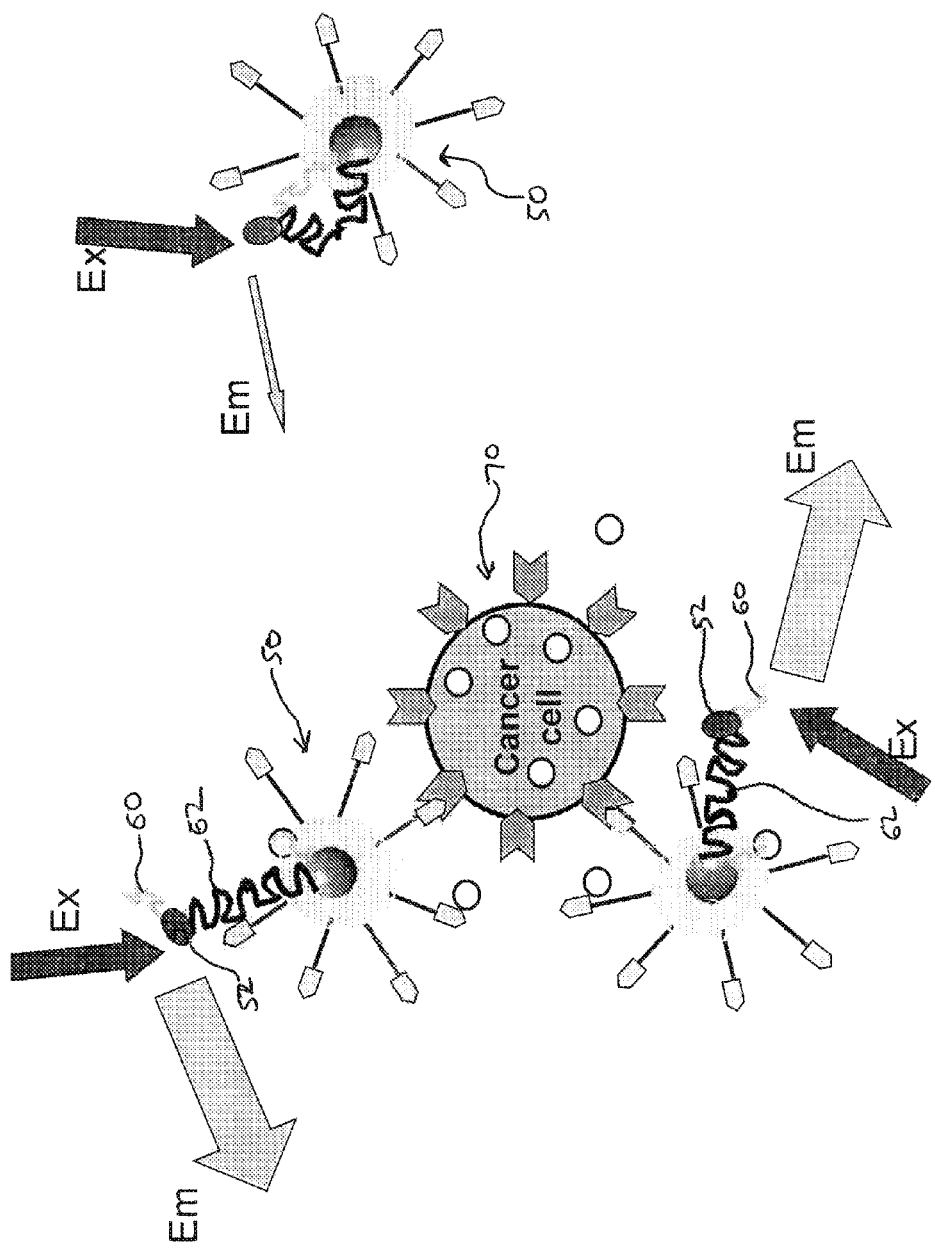
FIG. 7 shows a stage in operation of an inventive contrast marker, after enzymes from the cancer cell have cleaved the short spacer.

With the targeting molecule 64 associating with the receptor 72 on the target cell 70, an enzyme 56 secreted by the target cell cleaves the structure of the short spacer 60, as shown in FIG. 6. The distance between the fluorophore 52 and the NMP 54 assumes the spacing length provided by the long spacer 62 (e.g., the length of the long spacer). This results in an increase in the distance between the fluorophore (e.g., Cypate) 52 and the NMP 54 (FIG. 7), which (longer) distance provides fluorescence enhancement. Particularly, the fluorophore 52 receives excitation light Ex and emits light Em in NIR with much higher quantum yield (shown by the enlarged arrows in FIG. 7) and thus greatly improved fluorescence contrast. When excitation light is applied (e.g., NIR at 788 nm), the fluorescence of Cypate, consequently, can be emitted (e.g., NIR at 830 nm) at a highly enhanced level.

Figure 8A:
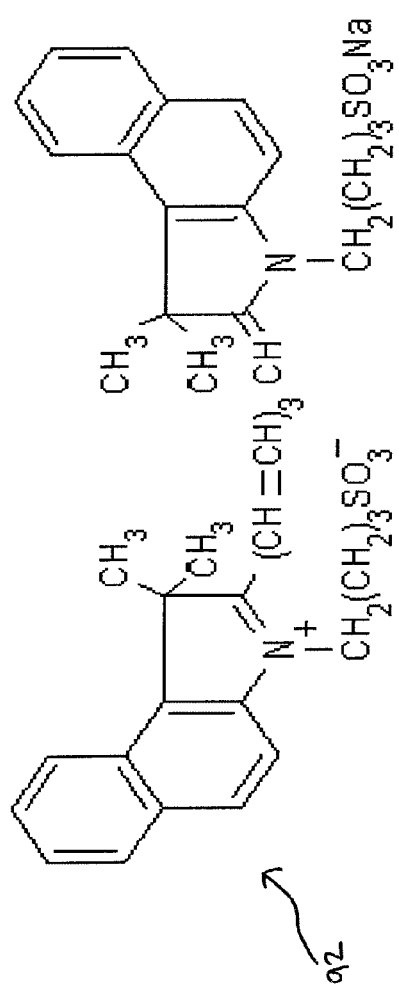
FIG. 8A shows Indocynanine Green (ICG)
Figure 8B:
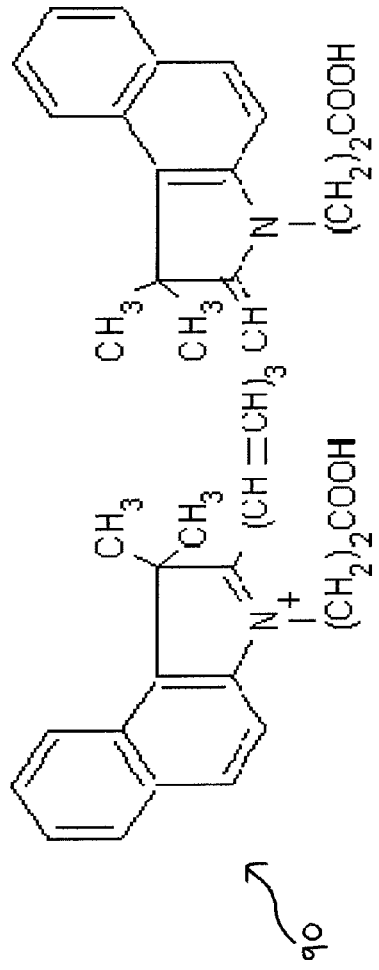
FIG. 8B shows Cypate, an ICG derivative.

An example fluorophore used is Cypate (shown as 90), shown in FIG. 8B, due to its enhancement capabilities and benefits. Cypate is a derivative of ICG (shown as 92), shown in FIG. 8A. Cypate has the advantage of being near infrared (NIR), having an excitation wavelength/emission wavelength (Ex/Em) of 780/830 nm. Cypate also provides a deeper penetration depth, but it has a low quantum yield (QY): 0.0028 in saline buffer, and 0.012 in blood. Nanogold particles (NGPs) are used for a fluorescence enhancer.

Figure 9:
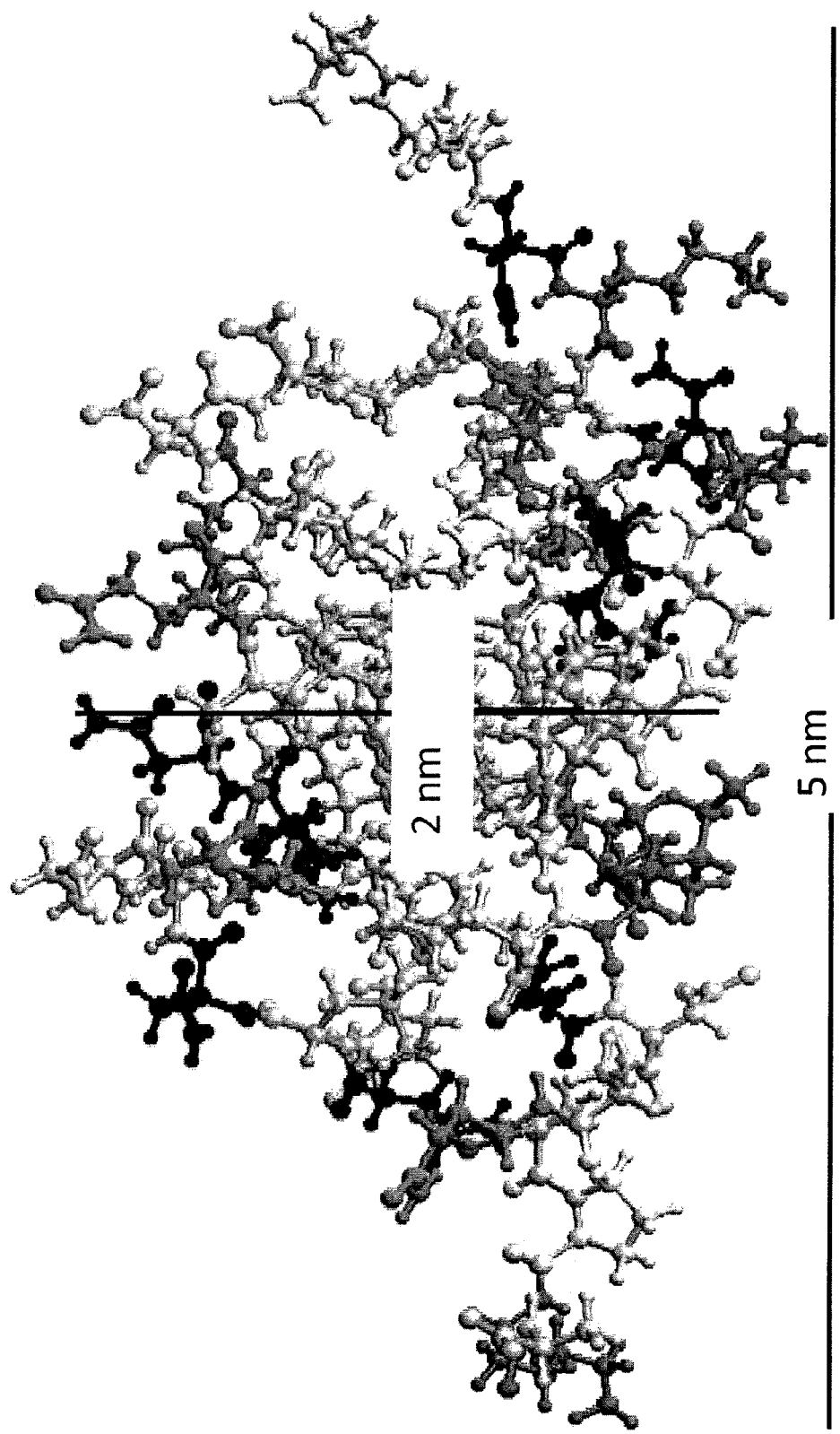
FIG. 9 shows a molecular simulation of Protein A.
Figure 10:
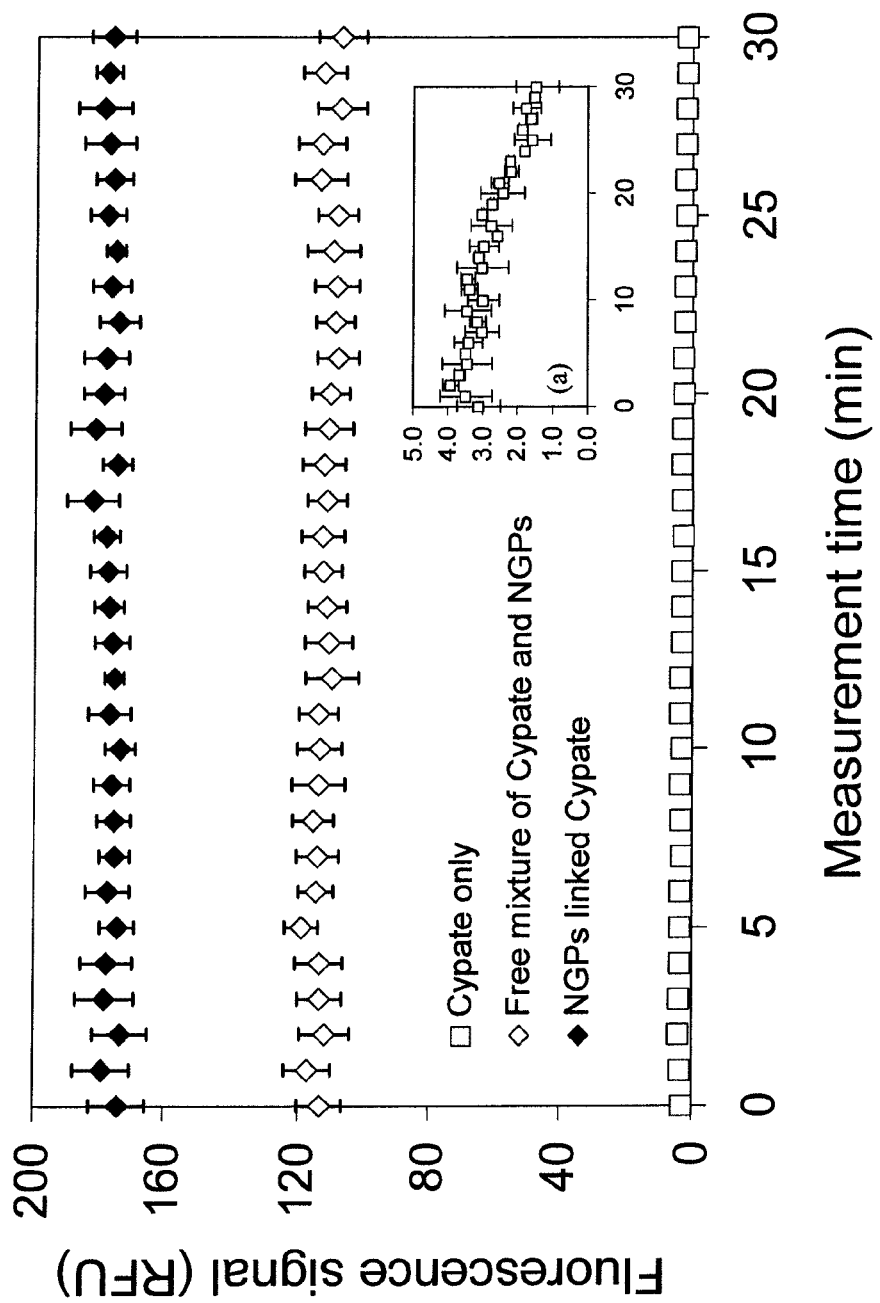
FIG. 10 shows fluorescence intensity and photostability of Cypate only, a free mixture of Cypate and NGPs, and NGPs linked to Cypate via Protein A.

A nonlimiting example spacer linking the Cypate and NGP is protein A, having a molecular weight (MW) of 40~60 kD. A molecular simulation of protein A is shown in FIG. 9. FIG. 10 shows example fluorescence intensity and photostability of Cypate only, a free mixture of Cypate and NGPs, and NGPs linked to Cypate via Protein A, where the Cypate concentration was 30 µM; 10 nmNGP-PA.

Figure 11:
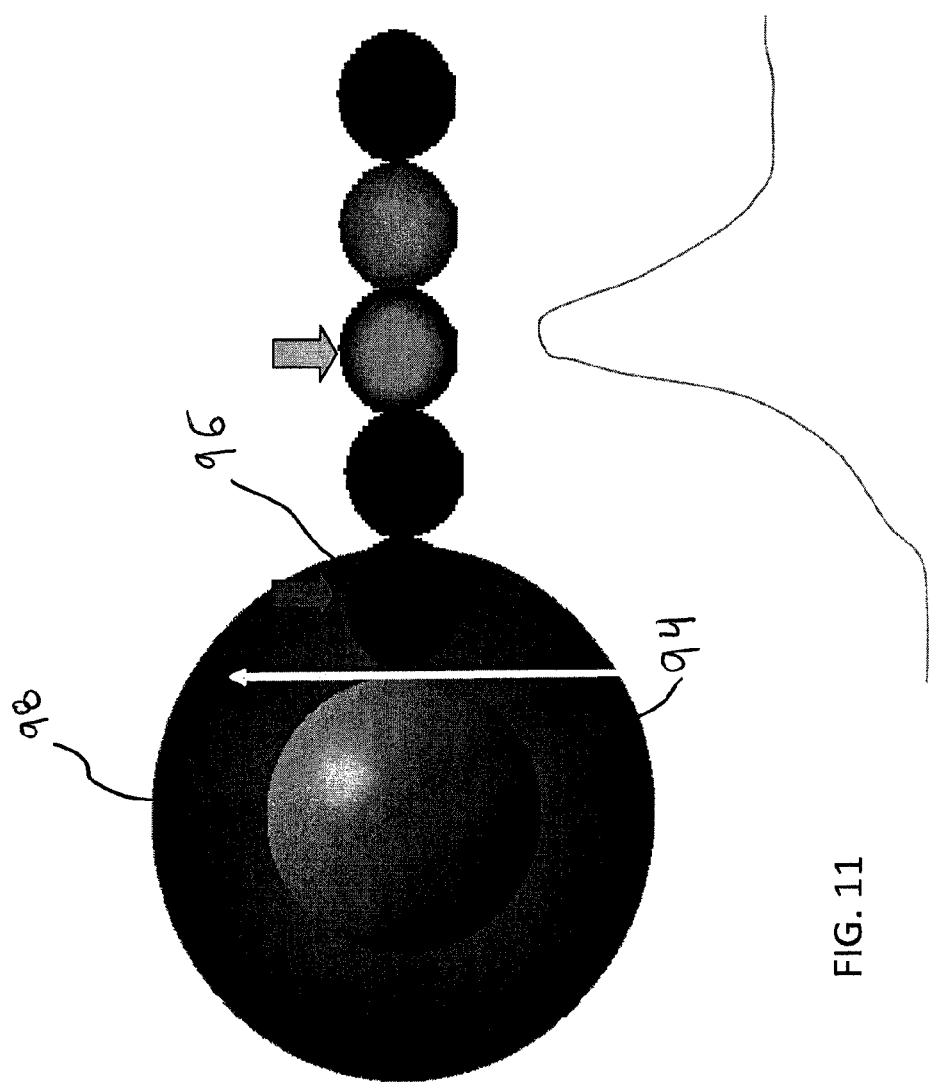
FIG. 11 shows an example of the effect of distance control from an NGP surface on Cypate fluorescence intensity.

FIG. 11 shows an example of the effect on distance control of an NGP surface 94 from Cypate 96 for both quenching and enhancement. As shown in FIG. 11, where the Cypate 96 is at a distance so as to be within the plasmon field 98 (preferably the distance provided by the short spacer) the fluorescence approaches zero. Beyond the plasmon field 98, the fluorescence rises to a peak, where the Cypate 96 is at an optimum distance (preferably, the distance provided by the long spacer). Beyond the optimum distance, the enhancing effect of the NGP 94 is reduced, until the effect is greatly reduced beyond a particular distance.

In an example embodiment for characterization of breast cancer, the short spacer is designed to be cleaved by urokinase-type plaminogen activator (uPA) because uPA is expressed in a number of highly invasive breast cancers. Another concern, which is related to testing the efficacy of the nano-contrast marker, is selection of the cancer targeting biomolecule. Among the many cancer-targeting elements known (e.g., folate, LHRH, etc.), an example targeting biomolecule that can be used is the PEG-linked tamoxifen moiety to bind the estrogen receptor (ER). Due to the modular nature of this contrast marker, the short chain cleavable-site and/or targeting-ligand can also be tailored for personalized medical applications.

As the metal nanoparticle size decreases to ~1 nm or smaller, the energy levels are so widely spaced that no plasmon can be generated, since free electrons are restricted to some isolated levels. Conversely, at particle sizes that are larger but still smaller than ~100 nm, the energy levels lie close to each other, and therefore, free electrons can jump easily among the energy levels to form a surface plasmon field. For a transitional size (1~3 nm), although the plasmon absorption band is not observed, there are still quite a few electrons that are transferred to the surface plasmon. In terms of practical utility, if the diameter of NMPs becomes greater than 30 nm, it is very difficult to disperse them in a solution and they tend to precipitate easily, although special surface treatment can prevent precipitation. Also, if the size of an entire nano-contrast marker is greater than 50 nm, it becomes difficult to deliver via bloodstream. Considering that other components (such as tumor targeting molecules, short and long spacers, and Cypate) can be conjugated onto the NMP, NMP sizes in the range between about 5 and 30 nm are preferred.

Figure 12:
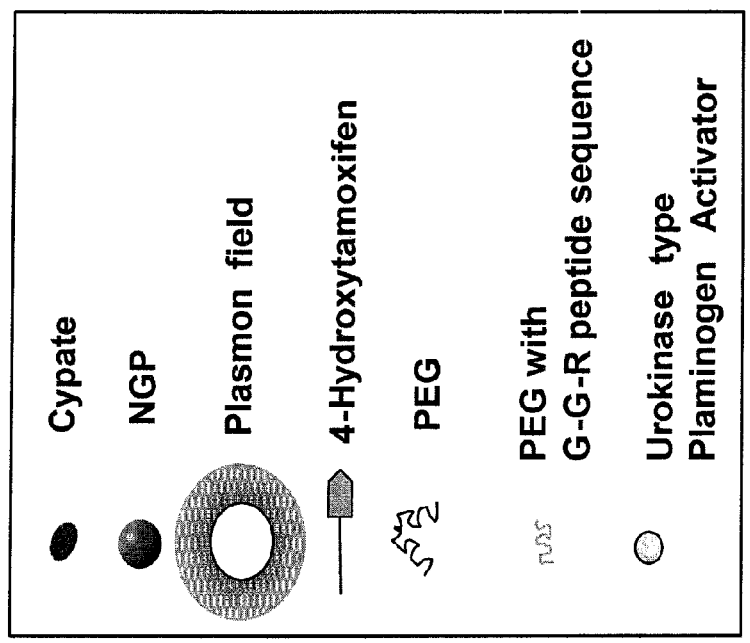
FIG. 12 shows an example contrast marker for targeting breast cancer cells, according to an embodiment of the present invention.
Figure 12:
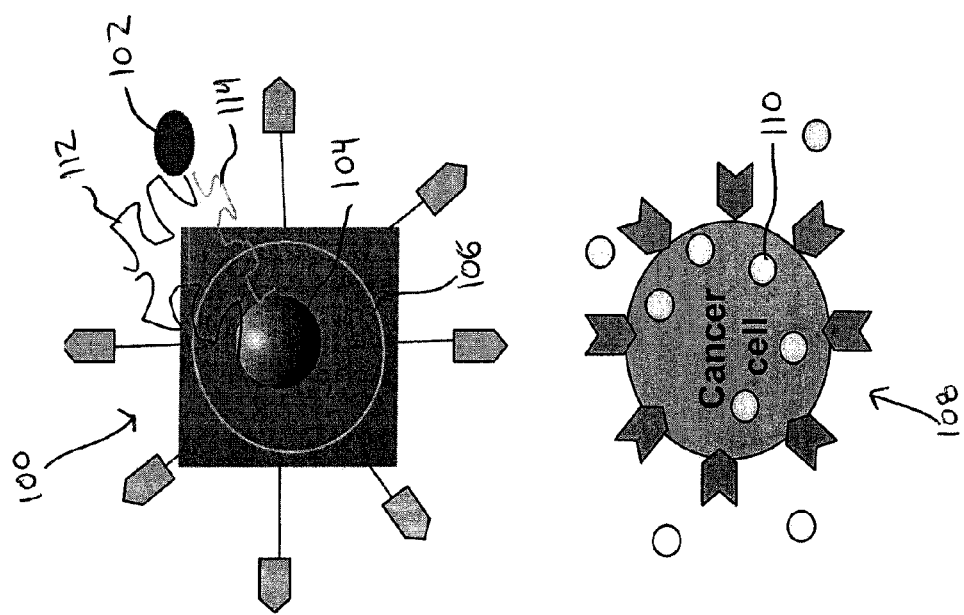

FIG. 12 shows an example assembled contrast marker 100 tailored for breast cancer detection. A Cypate fluorophore 102 is linked to an NGP 104, which has a particular plasmon field 106. The example target cell 108 is a cancer cell with an enzyme 110 embodied in a Urokinase type Plaminogen Activator. The targeting molecule for the example contrast marker 100 is 4-Hydroxytamoxifen. To bind the fluorophore 102 and the NGP 104, Poly(ethylene glycol) (PEG) is used for the long spacer 112, and PEG with G-G-R peptide sequence is used for the short spacer 114.

Figure 13:
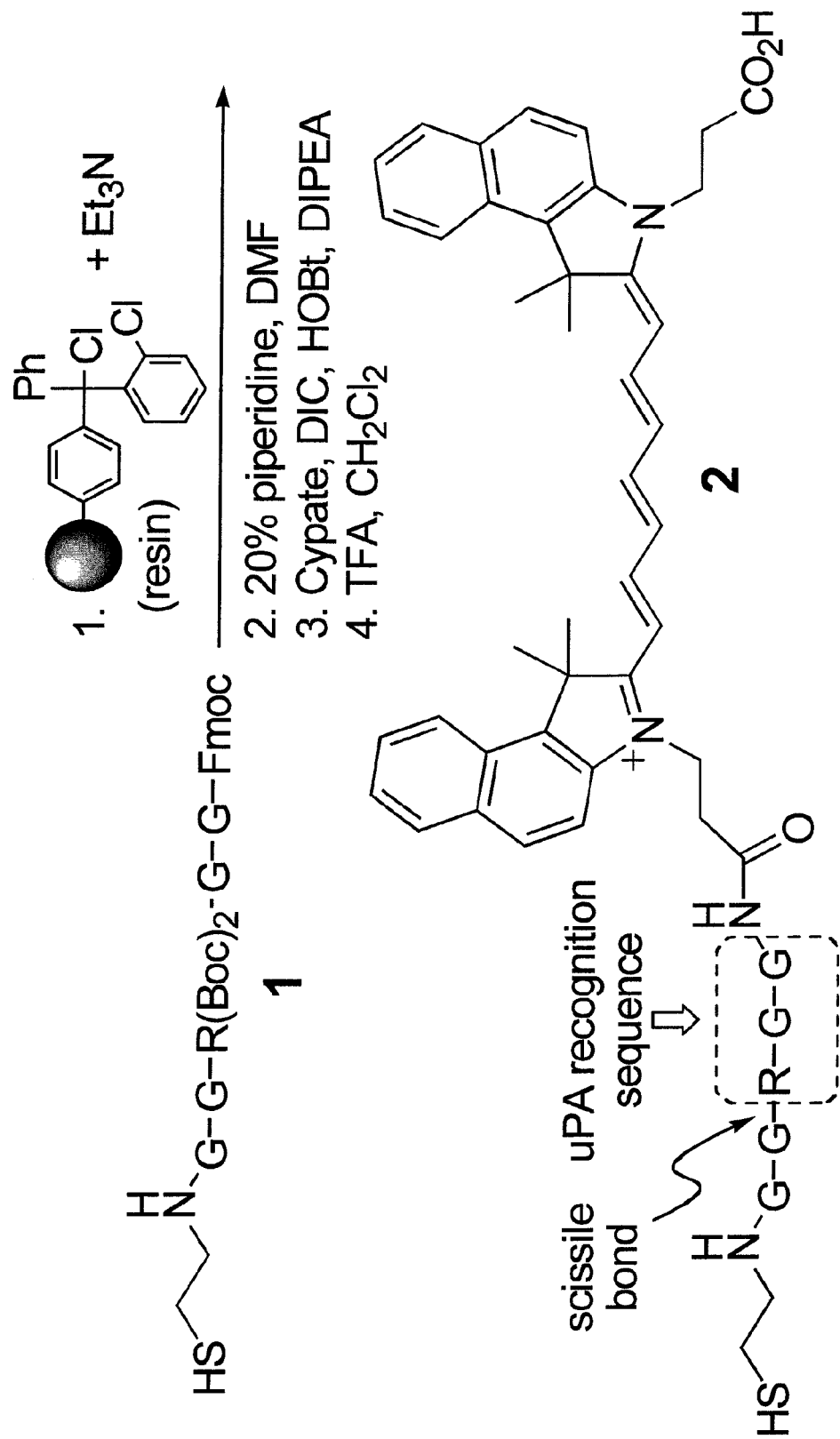
FIG. 13 shows peptides in an example synthesis featuring a G-G-R peptide sequence for uPA-mediated cleavage of a short spacer, according to an embodiment of the present invention.

A representative synthesis featuring the G-G-R peptide sequence for uPA-mediated cleavage of the short spacer 114 shown in FIG. 12 will now be discussed. Using solution phase methods (e.g., EDC and DIC couplings), the peptide 1 shown in FIG. 13 is prepared. Loading onto the commercially available trityl resin followed by Fmoc deprotection sets the stage for attachment of modified Cypate. The site isolation imparted by solid phase is particularly significant for success in the coupling of Cypate to the peptide, because Cypate contains two carboxylic acid moieties.

The short spacer length can be adjusted accordingly by either insertion or deletion of Gly residues adjacent to the uPA recognition sequence. Based on recent findings that caspase-3 cleaves a DEVD recognition sequence when attached to NMPs at a similar distance, the initially selected peptide motif 2 shown in FIG. 13 is an ideal starting point.

Figure 14:
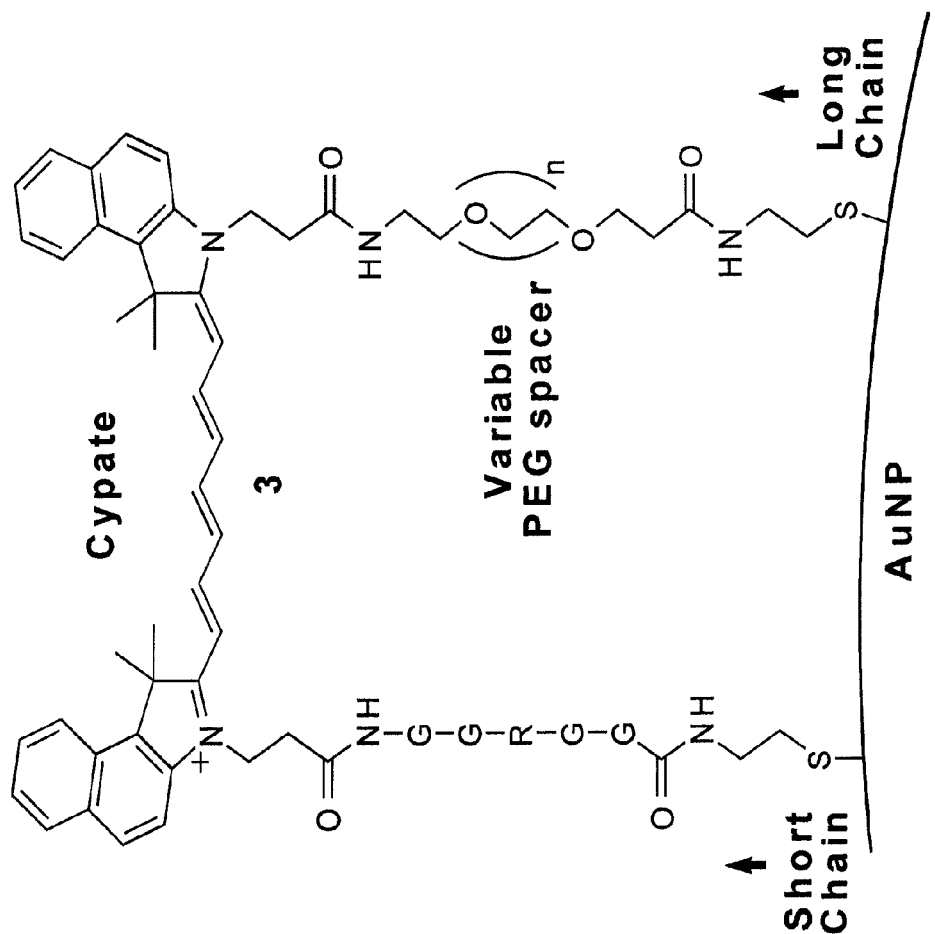
FIG. 14 shows a dual spacer Cypate analog according an embodiment of the present invention.

As shown in FIG. 12, an example long spacer can be Poly(ethylene glycol) (PEG), which can be adjusted in length to permit optimization of NMP-induced fluorescence enhancement. An example PEG starting material (Fmoc-NH-$PEG_n$-$CO_2H$, 16-88 atom amino PEG-acid spacers—from Novabiochem) can be capped with a thiol end (e.g., $H_2NCH_2CH_2SH$), Fmoc-deprotected, and then coupled to the resin-bound amino acid-Cypate conjugate from the scheme above. Release from the resin can afford the dual spacer Cypate analog 3 (shown in FIG. 14) suitable for direct attachment to NMPs.

After enzymatic cleavage of the short spacer at a cancer site, the longer PEG spacer can permit fluorophore extension away from the surface of the NMP. PEG is ideal for this application in that its function as a spacer moiety in aqueous media is understood in the art. High purity PEG derivatives (e.g., a,ω-diamines) with molecular weights up to 1500 Da (e.g., from BioVectra) can be incorporated as spacers to achieve lengths as needed (MW 3400 results in a nominal extension of 25 nm) For successful attachment of dual spacer analogs, such as 3, dilute concentration of NMP can be used initially to facilitate the conjugation of both spacers onto a single NMP. The fluorescence quenching and enhancement of NMP-3 analogues can be tested by incubation with uPA.

Figure 15:
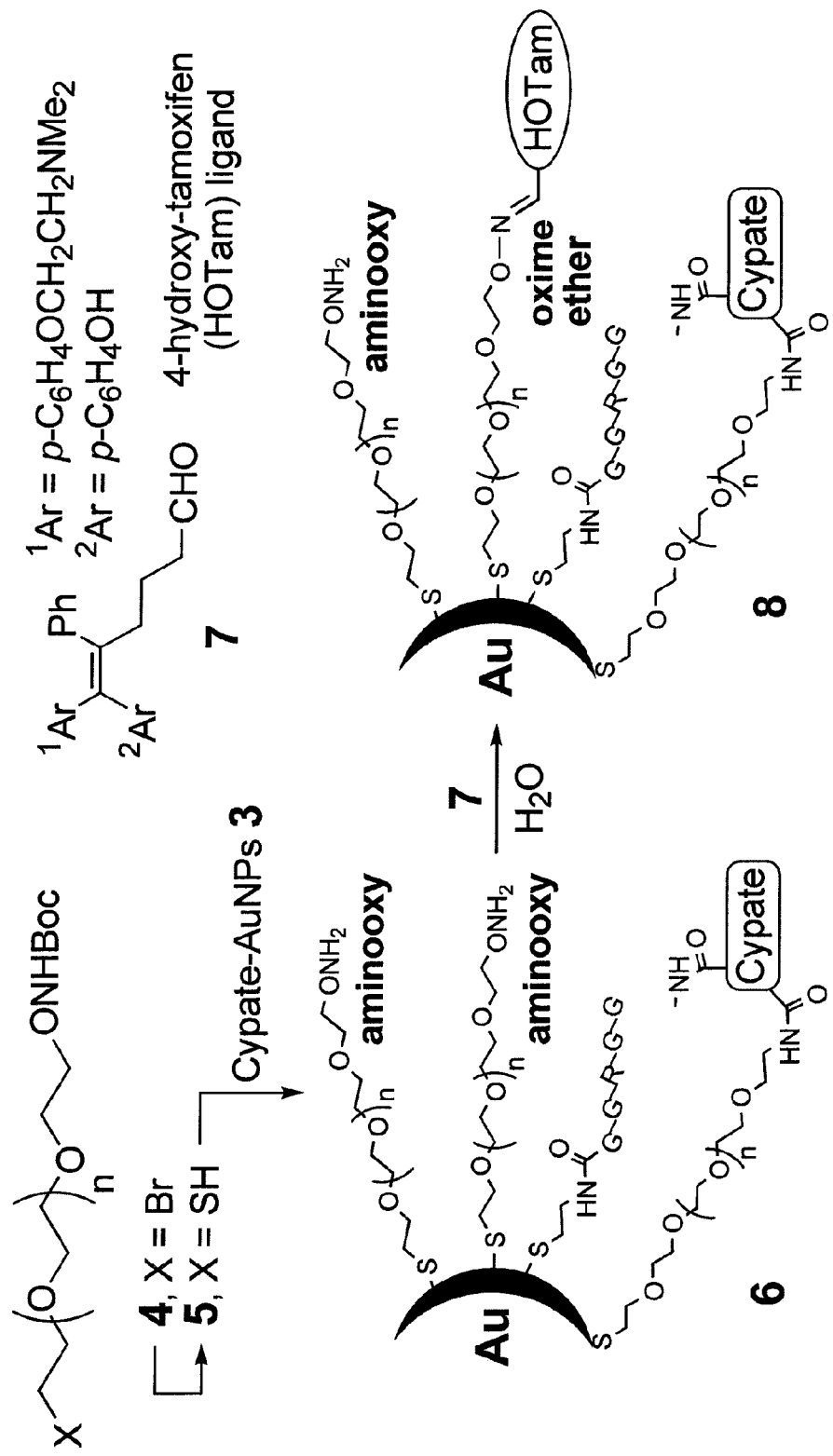
FIG. 15 shows additional analogs for the example synthesis.

Conversion of heterobifunctional aminooxy PEG reagents 4 to thiol analogs 5 (FIG. 15) enables a flexible strategy for attaching cancer-specific ligands to the NMP surface. Aminooxy reactions with aldehydes or ketones are an excellent means for the robust attachment of the targeting element. These condensations often proceed in near quantitative yield under aqueous conditions to provide oxime ether conjugates that are stable at physiological pH. The attachment of a targeting element to aminooxy-functionalized NMPs, such as 6, would require simple mixing with an aldehyde-modified ligand. This can be assisted with the aldehyde analog of 4-hydroxytamoxifen, aldehyde 7. 4-Hydroxytamoxifen is a potent competitor of β-estradiol ($E_2$) in binding the estrogen receptor (ER). While the ER is predominately localized in the nucleus with a fraction found in the cytoplasm, specific binding sites for $E_2$ at the plasma membrane make estrogen- and tamoxifen-based ligands popular choices for targeting breast cancer cells, particularly since 60-80% of female breast cancers over-express ER. HOTam-labeled Cypate-NMPs (e.g., 8) would have longer residency at the target tissue due to the specific ligand-ER interactions. This strategy can be adapted to incorporate multiple targeting elements by increasing the availability of surface aminooxy functionality (as shown in 8). In this way, aldehyde- or keto-modified peptide and antibody fragments can be attached to 8 to further increase its specificity for breast cancer. The fluorescence quenching and enhancement of NMP-(3+8) analogues also can be tested by uPA assays.

Figure 16:
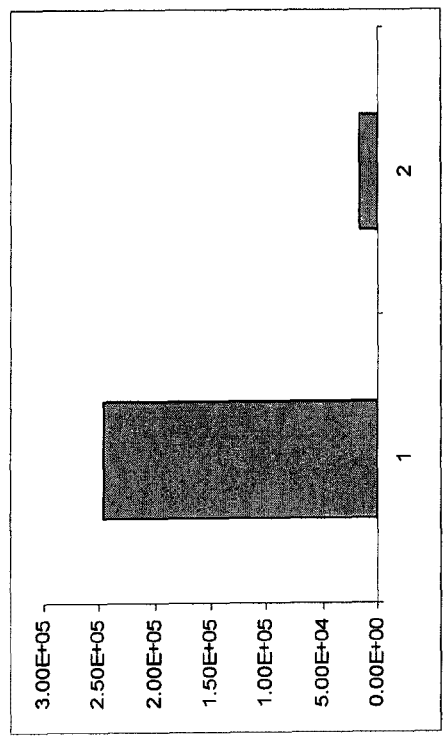
FIG. 16 shows fluorescence of Cypate by an NMP when Cypate is not conjugated to the NMP and fluorescence quenching when Cypate is conjugated to an NMP via a short linker.

Utilizing a nanogold particle (NGP), one of the NMPs that has a strong SPPF, one can either quench or enhance the fluorescence emission of a fluorophore, such as Cypate, by controlling the distance between a fluorophore molecule and an NGP according to the principles discussed above. The maximum level of fluorescence enhancement by an NMP is (1-QY), and therefore the potential for fluorescence enhancement of Cypate is very high, since the QY of Cypate is low. FIG. 16 shows fluorescence quenching of Cypate by an NMP 1) when Cypate is not conjugated to an NGP and 2) when Cypate is conjugated to an NGP via an 8-amino acid peptide chain.

Figure 17:
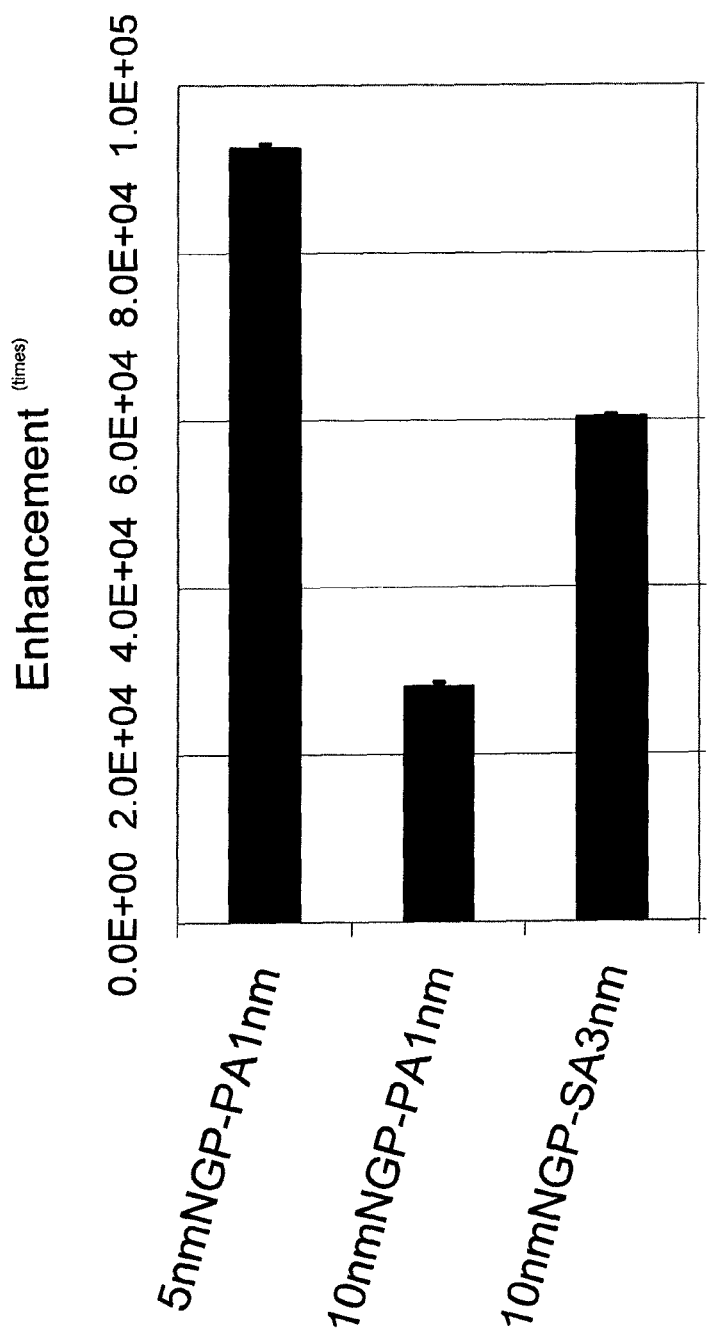
FIG. 17 shows Cypate flurorescence enhancement by 5 and 10 nm NMPs linked via protein A or streptavidin.

FIG. 17 shows Cypate fluorescence enhancement by 5 and 10 nm NMPs linked via protein A (PA) or streptavidin (SA). Among the three, 5 nm NMP-PA-Cypate was enhanced the most (900-fold). For 10 nm NMPs, the SA provided a higher enhancement than the PA.

Figure 18:
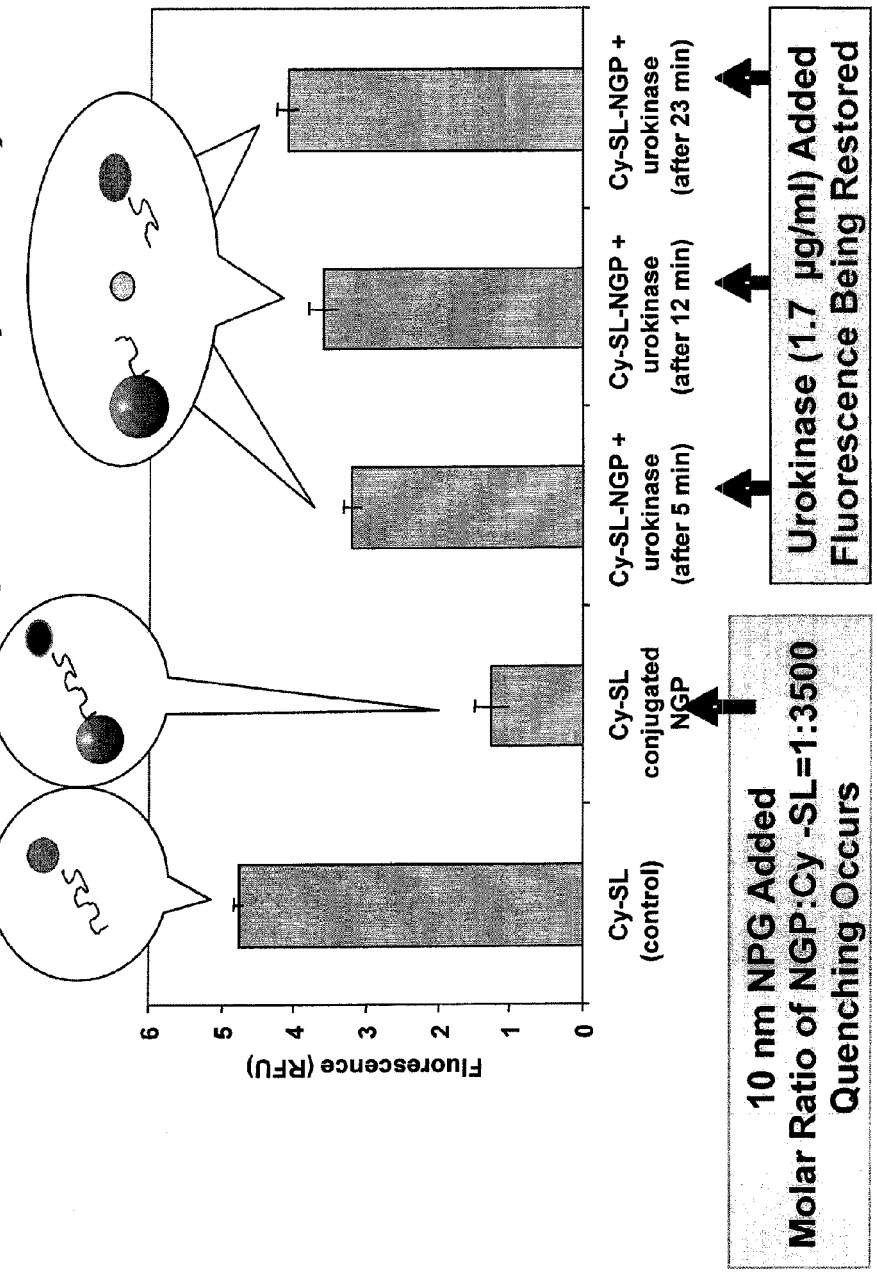
FIG. 18 shows fluorescence test results for Cypate and NGP linked by a short spacer having a G-G-G-R-G-G peptide sequence, indicating feasibility of the short spacer and restored fluorescence by cleaving the short spacer via an enzyme.

FIG. 18 shows fluorescence test results for Cypate and NPG linked by an example short spacer (short linker (SL)) (G-G-G-R-G-G peptide sequence). Cy-SL was used as a control. When 10 nm NGP was added (molar ratio of NGP:Cy-SL=1:3500), quenching occurs, significantly reducing the fluorescence. Urokinase (1.7 µg/ml) was then added to cleave the short spacer. After 5 minutes, the fluorescence was significantly restored, and fluorescence was additionally restored after 12 minutes and 23 minutes, illustrating that the short spacer can be cleaved with the enzyme to restore fluorescence of the Cypate fluorophore.

Figure 19:
FIG. 19 shows fluorescence test results for Cypate and NGP linked by a 4.5 nm long spacer.

FIG. 19 shows fluorescence test results for a first long spacer (long linker (LL)) (PEG n=11, ~4.5 nm) The NGP particle was 10 nm, and all samples were in a 0.001 M PBS buffer (Cy-$LL_{11}$: 2.7 µM; Cy-$LL_{11}$-NGP: NGP conc. 0.0263 µM, Cy conc. 2.7 µM). The conjugates were purified by dialysis. Results showed a fluorescence enhancement of 70.4%.

Figure 20:
FIG. 20 shows fluorescence test results for Cypate and NGP linked by a 10 nm long spacer.

For comparison, FIG. 20 shows fluorescence test results for an alternative long spacer (long linker (LL)) (PEG n=27, ~10 nm). The NGP particle was 10 nm, and all samples were in a 0.001 M PBS buffer (Cy-$LL_{27}$: 39 µM; Cy-$LL_{27}$-NGP: NGP conc. 0.025 µM, Cy conc. 39 µM). Again, the conjugates were purified by dialysis. Results showed a fluorescence enhancement of 12%, indicating that there is an optimum length for the long spacer for maximum fluorescence enhancement.

In another experiment, nanogold colloids (NGPs; 5 and 10 nm in citric and tannic acids) and Protein A conjugated NGP (NGP-PA) were obtained (Ted Pella, Redding, Calif., USA). L-glutathione (LG; Sigma/Aldrich; St. Louis, Mo., USA) was immobilized on the NGP surface using protocols as provided in Hong B, Kang K A (2006) Fluorescence enhancers for fluorophore mediated biosensors for cardiovascular disease diagnosis, Advances in experimental medicine and biology 578: 179-184; and Hong B, Kang K A (2006) Biocompatible, nanogold-particle fluorescence enhancer for fluorophore mediated, optical immunosensor, Biosensors and Bioelectronics, 21(7), 1333-1338, the disclosures of which are incorporated in their entirety herein by reference.

Cypate was covalently immobilized on the surface of the NGPs via LG (NGP-LG) or PA (NGP-PA) using protocols as provided in Kang K A, Hong B (2006) Biocompatible nanometal particle fluorescence enhancers, Critical Reviews in Eukaryotic Gene Expression 16(1), 45-60, which disclosure is incorporated in its entirety herein by reference. N,N' Dicyclohexylcarbodiimide (DCC; Sigma) was used to catalyze the reaction. First, Cypate and DCC was dissolved separately in a minimal amount of ethanol (<50 µl), the Cypate and DCC solutions were mixed at a molar ratio of 1:12, and immediately transferred to NGP-LG or NGP-PA solution. The mixture of Cypate and NGP-LG was stirred at room temperature for 30 min. For Cypate and NGP-PA, stirring was at 4° C. for 5 hours.

All samples (Cypate with and without NGP) were in a 0.001M PBS, and Cypate concentration was 30 µM, at which Cypate has maximum fluorescence. Fluorescence of samples was measured in 96-well EIA/RIA plate (Corning, N.Y., USA) using a fluorometer (Spectra Gemini XPS: Molecular Devices Corp., Sunnyvale, Calif., USA). The excitation and emission wavelengths were 780 and 830 nm, respectively.

Figure 21:
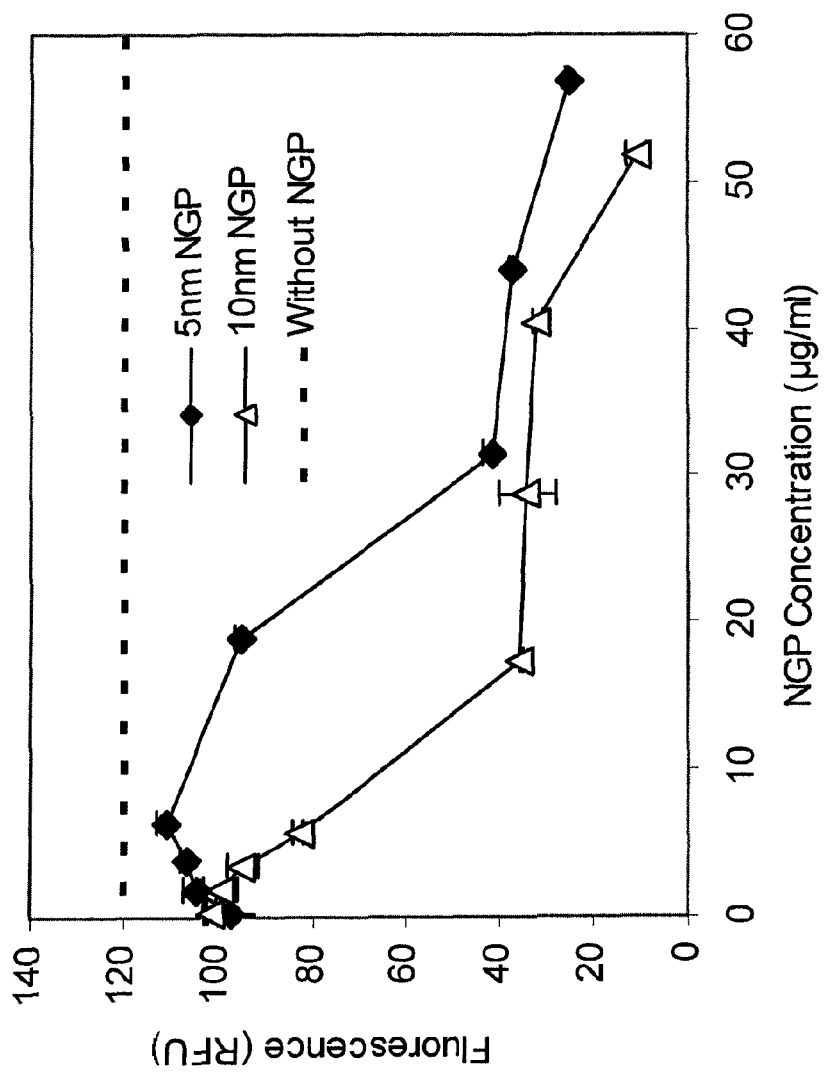
FIG. 21 shows fluorescence of Cypate without NGP, and quenched by NGPs of 5 and 10 nm.

The fluorescence was studied when Cypate was conjugated onto NGP surface (e.g., in bioimaging). LG (MW=307) was used as the short spacer, and its length had been estimated to be 1 nm. The fluorescence was observed when Cypate was conjugated to 5 and 10 nm NGPs via LG, at an NGP concentration range of 0~60 µg/ml, as shown in FIG. 21.

At all concentrations, the fluorescence decreased. In general, for higher concentration of NGP, more fluorescence was quenched. At the same wt concentration, 5 nm NGPs have binding sites (LG molecule numbers) twice of 10 nm NGPs. However, they quenched fluorescence less, probably because of the difference in SPPF strength for the different NGP size (that is, higher field strength for a larger particle size).

For 5 nm NGPs, at a very low concentration (<6 µg/ml), the quenching effect did not increase with the increase in NGP concentration, probably because only a portion of Cypate was conjugated to NGPs and most of Cypate were present in a free form in the solution.

Figure 22:
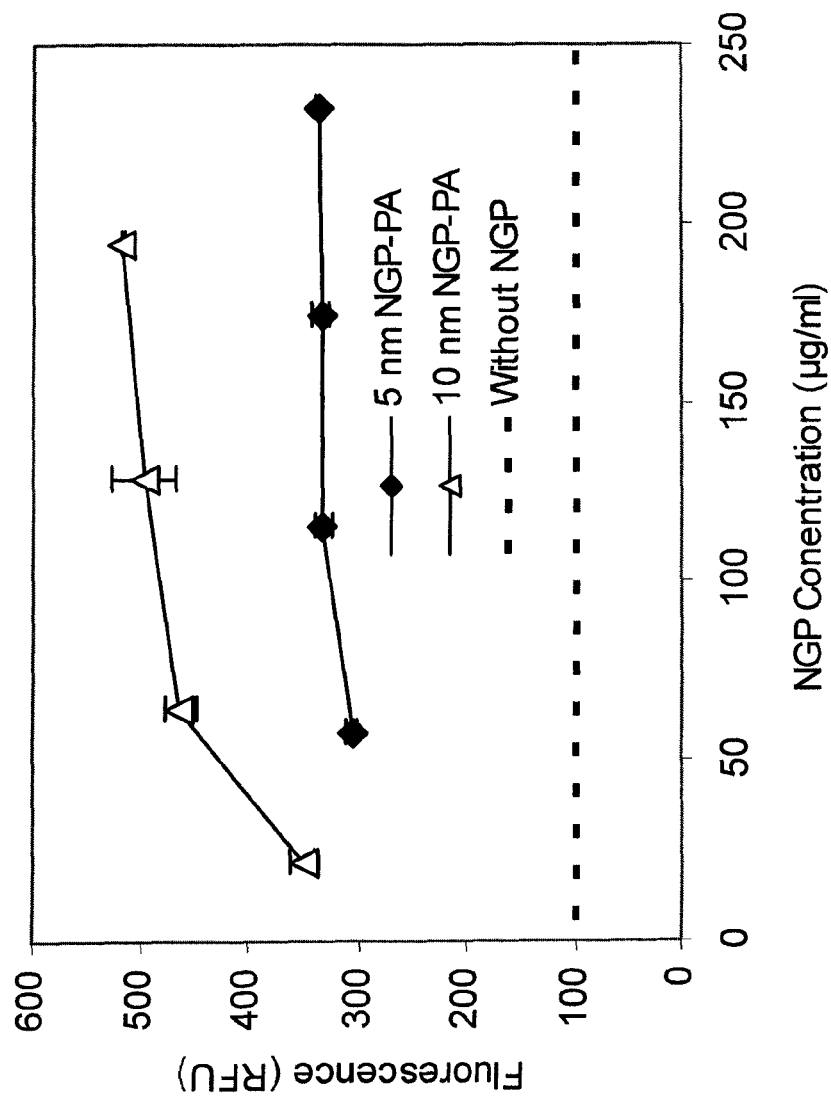
FIG. 22 shows fluorescence of Cypate enhanced by 5 and 10 nm NGPs linked by a protein A long spacer.

To study the fluorescence change by NGP with a longer spacer, Protein A (PA; MW 40~60 kD) was used as the spacer, as shown in FIG. 22. Since PA is a globular protein and it was unknown how the protein is conjugated on the NGP surface, it was difficult to estimate its length as a spacer, although simulation results suggest an estimated length of approximately 5 nm. The number ratios of PA to NGP were 4:1 and 16:1 for 5 and 10 nm NGPs, respectively. NGPs at a concentration range of 20~250 µg/ml were applied to Cypate solution.

The fluorescence of Cypate was enhanced extensively by both 5 and 10 nm NGPs. The enhancement was greater for a higher NGP concentration, especially for 10 nm NGPs. At the same weight concentration range, a 5 nm NGP has binding sites (PA molecule numbers) two times more than a 10 nm NGP does. However, it enhances fluorescence less than the 10 nm NGP does, confirming the difference in the SPPF strength for different-sized particles.

Using the SPPF of NMPs, artificial fluorescence alteration of Cypate (NIR fluorophore) was achieved. With manipulating the distance between an NGP and a fluorophore by placing a molecular spacer between them, up to 90% of fluorescence quenching and 500% enhancement were achieved. The level of quenching and enhancement may be optimized to provide a fluorophore-nanoparticle complex for highly site-specific localization, such as but not limited to highly specific breast cancer localization.

Thus, embodiments of the present invention provide, among other things, highly target cell-specific contrast markers for bioimaging as well as methods for bioimaging using such contrast markers, having various features and advantages. An example contrast marker emits fluorescence at a much higher quantum yield. However, the dual mechanisms of the long spacer and the short spacer ensure the fluorescence contrast only for the target cell (e.g., cancer cell). This in turn increases the specificity for the target cell, with minimal noise. Embodiments of the present invention employ both the fluorescence quenching and fluorescence enhancement features in a single contrast marker and bioimaging method, uniquely taking advantage of both properties, as opposed to known methods that attempt to employ only the quenching feature or alternatively only the enhancing feature. The fluorescence is also easier to produce. By tailoring the contrast marker, e.g., by tailoring the fluorophore and/or the targeting biomolecule for a particular target cell, personalized medical detection and/or diagnosis can be provided. By adding therapeutic components to the contrast marker, such as but not limited to cancer drugs, nanoparticle-mediated hyperthermia, photodynamic therapeutics, etc., seamless diagnosis and treatment are possible.

Though more particular example contrast markers and target cells have been shown and described herein with regard to breast cancer, it is to be understood that embodiments of the present invention may be applied to characterization of other cancer cells or even target cells for other diseases. Example methods for tailoring the specificity of such contrast markers are provided herein. The invention is not limited to detection or diagnosis of breast cancer, or even cancer in general.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

The invention claimed is:

1. A contrast marker for indicating a presence of a target cell in an environment, the contrast marker comprising:
   a fluorophore;
   a nanometal particle (NMP);
   a short spacer and a long spacer, each directly linking said fluorophore to said NMP, wherein said short spacer holds said fluorophore at a quenching distance from said NMP and said long spacer holds said fluorophore at a fluorescence enhancing distance from said NMP;
   wherein said NMP is coated with a targeting biomolecule configured to engage the target cells; and
   wherein said short spacer is configured to be cleaved by a molecule characterizing the target cells;
   whereby, before said short spacer is cleaved, said short spacer controls a distance between said fluorophore and said NMP to be the quenching distance, so that the fluorescence is quenched; and
   whereby, after said short spacer is cleaved, said long spacer controls the distance between said fluorophore and said NMP to be the fluorescence enhancing distance, so that the fluorescence is enhanced.

2. The contrast marker of claim 1, wherein said long spacer is configured to be biologically stable in the environment.

3. The contrast marker of claim 2, wherein said NMP comprises a nano-sized gold particle (NGP).

4. The contrast marker of claim 3, wherein the molecule characterizing the target cells comprises an enzyme secreted by the target cells.

5. The contrast marker of claim 4, wherein said fluorophore comprises a derivative of Indocyanine Green (ICG).

6. The contrast marker of claim 4, wherein said long spacer comprises a biocompatible polymer.

7. The contrast marker of claim 6, wherein said long spacer comprises Poly(ethylene glycol) (PEG).

8. The contrast marker of claim 7, wherein said short spacer comprises PEG having a G-G-R peptide sequence.

9. The contrast marker of claim 4, wherein the target cell comprises a cancer cell.

10. The contrast marker of claim 9, wherein said targeting biomolecule is selected from the group consisting of antibodies and aptamers.

11. A method for detecting a presence of a target cell in an environment, the method comprising:
  providing the contrast marker of claim 1 in the environment containing the target cell;
  applying an excitation light to the contrast marker; and
  detecting fluorescence emitted from the contrast marker, thereby detecting the presence of the target cell in the environment;
  whereby, before the short spacer is cleaved, the short spacer controls a distance between the fluorophore and the NMP to be the quenching distance, so that the fluorescence is quenched; and
  whereby, after the short spacer is cleaved, the long spacer controls the distance between the fluorophore and the NMP to be the fluorescence enhancing distance, so that the fluorescence is enhanced.

12. The method of claim 11,
  wherein the targeting biomolecule is configured to engage with a receptor of the target cell; and
  wherein, when the targeting biomolecule engages the receptor, the enzyme cleaves the short spacer.

13. The method of claim 12, wherein the target cell is a cancer cell.

14. The method of claim 12, wherein the fluorophore comprises a derivative of Indocyanine Green (ICG).

15. The method of claim 14, wherein the fluorophore comprises Cypate.

16. The method of claim 11, wherein the providing comprises introducing the contrast marker into a blood stream of a patient.

17. A cancer contrast marker, comprising a fluorophore directly linked to a nanometal particle (NMP) by both a short spacer and a long spacer, wherein the short spacer holds the fluorophore at a quenching distance from the NMP and can be cleaved by enzymes secreted by cancer cells, and the long spacer holds the fluorophore at a fluorescence enhancing distance from the NMP;
  wherein before the short spacer is cleaved, the short spacer controls a distance between said fluorophore and the NMP to be the quenching distance, so that the fluorescence is quenched; and
  wherein after the short spacer is cleaved, the long spacer controls the distance between the fluorophore and the NMP to be the fluorescence enhancing distance, so that the fluorescence is enhanced.

* * * * *

UNITED STATES PATENT AND TRADEMARK OFFICE
CERTIFICATE OF CORRECTION

PATENT NO. : 8,758,727 B2  
APPLICATION NO. : 12/935336  
DATED : June 24, 2014  
INVENTOR(S) : Kang et al.

Page 1 of 1

It is certified that error appears in the above-identified patent and that said Letters Patent is hereby corrected as shown below:

In the Specification:

Col. 3, line 64        Please insert a --.-- after "quenching".

Signed and Sealed this  
Seventh Day of April, 2015

Michelle K. Lee  
*Director of the United States Patent and Trademark Office*